(12) United States Patent
Nanton et al.

(10) Patent No.: US 11,903,964 B2
(45) Date of Patent: Feb. 20, 2024

(54) FECES BINDER IN FEED FOR FISH

(71) Applicant: CAN TECHNOLOGIES, INC., Wayzata, MN (US)

(72) Inventors: Dominic Andre Nanton, Sandnes (NO); Peter Bjorn Rugroden, Otsego, MN (US); Kari Juhani Ruohonen, Turku (FI); Marc Turano, Wilmington, NC (US); Terje Utne, Stavanger (NO)

(73) Assignee: CAN TECHNOLOGIES, INC., Wayzata, MN (US)

( * ) Notice: Subject to any disclaimer, the term of this patent is extended or adjusted under 35 U.S.C. 154(b) by 0 days.

(21) Appl. No.: 17/818,073

(22) Filed: Aug. 8, 2022

(65) Prior Publication Data

US 2023/0263823 A1   Aug. 24, 2023

Related U.S. Application Data

(63) Continuation of application No. PCT/US2022/070725, filed on Feb. 18, 2022.

(60) Provisional application No. 63/158,772, filed on Mar. 9, 2021, provisional application No. 63/151,269, filed on Feb. 19, 2021.

(51) Int. Cl.
*A61K 31/736* (2006.01)
*A23K 20/147* (2016.01)
*A23K 20/163* (2016.01)
*A23K 50/80* (2016.01)
*A23K 10/30* (2016.01)
*A61K 9/00* (2006.01)

(52) U.S. Cl.
CPC ............ *A61K 31/736* (2013.01); *A23K 10/30* (2016.05); *A23K 20/147* (2016.05); *A23K 20/163* (2016.05); *A23K 50/80* (2016.05); *A61K 9/0056* (2013.01)

(58) Field of Classification Search
CPC .. A61K 31/736; A61K 9/0056; A23K 20/147; A23K 50/80; A23K 10/30
USPC .......................................................... 514/54
See application file for complete search history.

(56) References Cited

U.S. PATENT DOCUMENTS

| 5,773,051 | A | 6/1998 | Kim |
| 2009/0011089 | A1 | 1/2009 | Brinker |
| 2017/0295826 | A1 | 10/2017 | Buttle |
| 2021/0051982 | A1* | 2/2021 | Brinker .................. A23K 40/25 |

FOREIGN PATENT DOCUMENTS

| CN | 100459969 | C | * | 2/2009 |
| CN | 109123245 | A | | 1/2019 |
| CN | 109123246 | A | | 1/2019 |
| GB | 2374514 | A | * | 10/2002 |
| NO | 323529 | B1 | | 6/2007 |
| NO | 20160674 | A1 | | 10/2017 |
| WO | WO 8704051 | | * | 7/1987 |

OTHER PUBLICATIONS

Utz et al.; CN 100459969 C; Feb. 11, 2009 (Machine-English Translation).*
Wright (Gobal Seafood Alliance; Mar. 13, 2017).*
Brinker, A., et al., 2005, "Optimised effluent treatment by stabilized trout faeces," Aquaculture 249, 125-144.
Zhu, S., et al., 2001. "Effects of organic carbon on nitrification rate in fixed film biofilters," Aquacult. Eng. 25(1), 1-11.
Cripps, S.J., et al., 2000, "Solids management and removal for intensive land-based aquaculture production systems," Aquacult. Eng. 22, 33-56.
Davidson, J., et al., 2009, "Heavy metal and waste metabolite accumulation and their potential effect on rainbow trout performance in a replicated water reuse system operated at low or high flushing rates," Aquacult. Eng. 41, 136-145.
Davidson, J., et al., 2011, "The effects of ozone and water exchange rates on water quality and rainbow trout *Oncorhynchus mykiss* performance in replicated water recirculating systems." Aquacult. Eng. 44, 80-96.
Davidson, J., et al., 2016, "Schroyer, K., Summerfelt, S., 2016b. Effects of feeding a fishmeal-free versus a fishmeal-based diet on post-smolt Atlantic salmon *Salmo salar* performance, water quality, and waste production in recirculation aquaculture systems," Aquacult. Eng. 74, 38-51.
Fernandes, P.M., et al., 2014 "Daily microparticle distribution of an experimental recirculating aquaculture system—a case study," Aquacult. Eng. 60, 28-34.
Foroutani, M.B. et al., 2018 "Minimizing marine ingredients in diets of farmed Atlantic salmon (*Salmo salar*): Effects on growth performance and muscle lipid and fatty acid composition," PLoS ONE 13(9): e0198538.
Liltved, H., et al., 1999. "Removal of particle associated bacteria by prefiltration and ultraviolet irradiation." Aquacult. Res. 30, 445-450.
Patterson, R.N., et al, 2003. "Micro-particles in recirculating aquaculture systems: particle size analysis of culture water from a commercial Atlantic salmon site." Aquacult. Eng. 28, 99-113.
Brinker, "Guar gum in rainbow trout (*Oncorhynchus mykiss*) feed: The influence of quality and dose on stabilisation of faecal solids", Aquaculture, 2007, 267, 315-327. (Year: 2007).
Brinker, A., et al., 2012, "Fish meal replacement by plant protein substitution and guar gum addition in trout feed. Part II: Effects on faeces stability and rheology," Biorheology 49(1), 27-48.
Database WPI, Week 201914, Thomson Scientific, London, GB; AN 2019-05035D XP002806639, & CN 109 123 245 A (Univ Chongqing Arts & Sci) Jan. 4, 2019, abstract, 2 pages.

(Continued)

*Primary Examiner* — Yih-Horng Shiao

(57) ABSTRACT

The present disclosure generally relates to a fish feed or fish feed product including a binding agent that increases the particle size and stability of feces produced by fish that consume the fish feed or fish feed product. In general, the fish feed will include a binding against such as locust bean gum, cassia gum, xanthan gum, tara gum, or combinations thereof. Also provided are methods for increases fish feces stability and methods for eliminating suspended solids from a recirculating aquaculture system.

22 Claims, 19 Drawing Sheets

(56) References Cited

OTHER PUBLICATIONS

Database WPI, Week 201926, Thomson Scientific, London, GB; AN 2019-05035C XP002806640, & CN 109 123 246 A (Univ Chongqing Arts & Sci) Jan. 4, 2019, abstract, 2 pages.

Letelier-Gordo, et al., "Reducing the dietary protein:energy (P:E) ratio changes solubilization and fermentation of rainbow trout (*Oncorhynchus mykiss*) faeces," Aquaculture Engineering, 66, 2015, 22-29.

Reid, et al., "A review of the biophysical properties of salmonid faeces: implications for aquaculture waste dispersal modes and integrated multi-trophic aquaculture," Aquaculture Research, 2009, 40, 257-273.

\* cited by examiner

US 11,903,964 B2

FECES BINDER IN FEED FOR FISH

CROSS REFERENCE TO RELATED APPLICATIONS

This application is a Continuation of International Application No. PCT/US2022/070725, filed Feb. 18, 2022, which claims the benefit of U.S. Provisional Application No. 63/151,269, filed Feb. 19, 2021, and U.S. Provisional Application No. 63/158,772, filed Mar. 9, 2021, each of which is incorporated herein by reference in its entirety.

FIELD OF THE INVENTION

The invention relates to fish feed, methods for increasing the particle size and stability of feces produced by a fish fed the fish feed, and to methods for reducing the content of undesired nutrients in water discharged from a fish farm.

BACKGROUND OF THE INVENTION

Recirculating aquaculture systems (RAS) have grown in prevalence for land-based rearing of fish. For example, RAS may be used to produce salmon smolt as well as grow salmon to market size. RAS operates by filtering the water extracted from the fish tanks prior to recirculation in the tank or release into the environment. Both fresh water, brackish and saltwater RAS are known and used in the art. The RAS technology provides many benefits over traditional fish farming methods, including reduced regulatory burdens, reduced shipping costs by locating the fish production close to markets, minimizing environmental risks related to storms, algae blooms, and natural threats, and increasing control over the culture environment to mimic the biology of the cultured species from optimal performance.

However, adoption of the RAS technology brings new challenges. Metabolic waste including suspended solids and fine particles accumulate in the system, which may cause damage to fish gills, jeopardize fish health by providing substrate for pathogens, reduce efficiency of the systems recirculation and biofilters, increased burden on water filtration processes, and the like. Removal of metabolic waste, suspended solids, and fine particles is also an issue for many other land-based farms as well as open, semi-closed, and closed sea pens.

Therefore, a need in the art exists for additional compositions and methods to control and help eliminate suspended solids in RAS as well as other fish rearing and fish farming systems.

SUMMARY OF THE INVENTION

Provided herein is an extruded, pressed, or particulate fish feed comprising between about 0.2% to about 2.0% by weight of a binding agent comprising at least of one psyllium husk, xanthan gum, and a galactomannan polysaccharide comprising an average mannose to galactose ratio of 3:1 to 5:1. The galactomannan polysaccharide may comprise tara gum, locust bean gum, cassia gum, or combinations thereof. The fish feed may be a feed for a carnivorous fish. The fish feed may be a salmonid feed. The fish feed may comprise between about 15% and about 65% protein and between about 10% and about 45% fat. The feed may comprise land-animal protein, fishmeal, plant-based protein, or combinations thereof. The fish feed may comprise fishmeal and a land-animal protein. The fish feed may comprise fishmeal and a plant-based protein. The fish feed may comprise fishmeal, a land-animal protein, and a plant-based protein. The fish feed may comprise at least 0.1 mg astaxanthin per kg of feed. The fish feed may comprise between 0.5% and 1.5% of the binding agent. The fish feed may comprise between 0.2% and 0.5% of the binding agent. The fish feed may comprise between 0.5% and 1.0% of the binding agent. The binding agent may be or may comprise locust bean gum.

Also provided is an extruded, pressed, or particulate fish feed comprising between about 0.2% to about 2.0% by weight of a binding agent selected comprising at least one of psyllium husk, xanthan gum, and a galactomannan polysaccharide comprising an average mannose to galactose ratio of 3:1 to 5:1, between about 30% and about 50% by weight protein, and about 15% to about 30% by weight fat. The fish feed may be a feed for a carnivorous fish. The fish feed may be in the form of pellets having a feed size suitable for a salmonid. The galactomannan polysaccharide may comprise at least one of tara gum, locust bean gum, and cassia gum. The binding agent may be or may comprise locust bean gum.

Also provided is a method for feeding a fish, the method comprising feeding a fish any of the fish feeds as described herein.

Also provided is a method for reducing suspended solids in rearing water of a fish farm, the method comprising feeding to a fish in the fish farm any of the fish feeds described herein, wherein suspended solids in the rearing water are reduced relative to the suspended solids in the rearing water of a fish fed a feed without the binding agent. The fish farm may be a recirculation aquaculture system. The fish may be a salmonid. Suspended solids in the rearing water may be reduced by at least 50% relative to the suspended solids in the rearing water of a fish fed a feed without the binding agent.

Also provided is a method for decreasing undesired nutrients in water discharged from a fish farming system, the method comprising feeding to a fish in the fish farming system any of the fish feeds described herein, wherein undesired nutrients in water discharged from the fish farming system are reduced relative to the water discharged from an equivalent fish farming system in which the fish are fed an equivalent feed lacking the binding agent. The fish may be a salmonid. The fish farm system may be a recirculation aquaculture system. The undesired nutrients may be reduced by at least 50%.

Also provided is a method for increasing feces removal from a fish farm, the method comprising, feeding to a fish in the fish farm any of the fish feeds described herein; and removing or causing to have removed feces from the fish farm, wherein feces removal is increased relative to feces removal from an equivalent fish farm in which fish are fed a feed without the binding agent. The feces may be removed by filtration or settling. The feces may be removed by mechanical filtration with a pore size of 60 μm or less. The fish farm may be a recirculation aquaculture system. The fish may be a salmonid.

Also provided is a method for increasing the size of feces produced by a fish in a fish farm, the method comprising feeding to the fish in the fish farm a fish feed comprising between about 0.2% to about 2.0% by weight of a binding agent comprising at least one of psyllium husk, xanthan gum, and a galactomannan polysaccharide comprising an average mannose to galactose ratio of 3:1 to 5:1, wherein the average size of feces produced by the fish in the fish farm is larger than the average size of feces produced by an equivalent fish that has been fed an equivalent feed lacking the binding agent. The galactomannan polysaccharide may comprise tara gum, locust bean gum, cassia gum, and combinations thereof. The fish may be a carnivorous fish. The fish may be a salmonid. The fish feed may comprise between about 15% and about 65% protein and between about 10% and about 45% fat. The feed may comprise land-animal protein, fishmeal, plant-based protein, or combinations thereof. The fish feed may comprise fishmeal and a land-animal protein. The fish feed may comprise fishmeal and a plant-based protein. The fish feed may comprise fishmeal, a land-animal protein, and a plant-based protein. The fish feed may comprise at least 0.1 mg astaxanthin per kg of feed. The fish feed may comprise between 0.5% and 1.5% of the binding agent. The fish feed may comprise between 0.2% and 0.5% of the binding agent. The fish feed may comprise between 0.5% and 1.0% of the binding agent. The fish farm may be a recirculation aquaculture system. The feces with increased size may also have increased mechanical strength and increased shear resistance. The feces size may increase by at least 10%.

BRIEF DESCRIPTION OF THE DRAWINGS

(FIG. 9A) Supranuclear vacuole score of 1 (left) and 4 (right); (FIG. 9B) Eosinophilic granular cell infiltration of the submucosa, score of 2 (left); densely infiltrated granular cell infiltration of the mucosa, score of 4 (right)

DETAILED DESCRIPTION OF THE INVENTION

Figure 1:
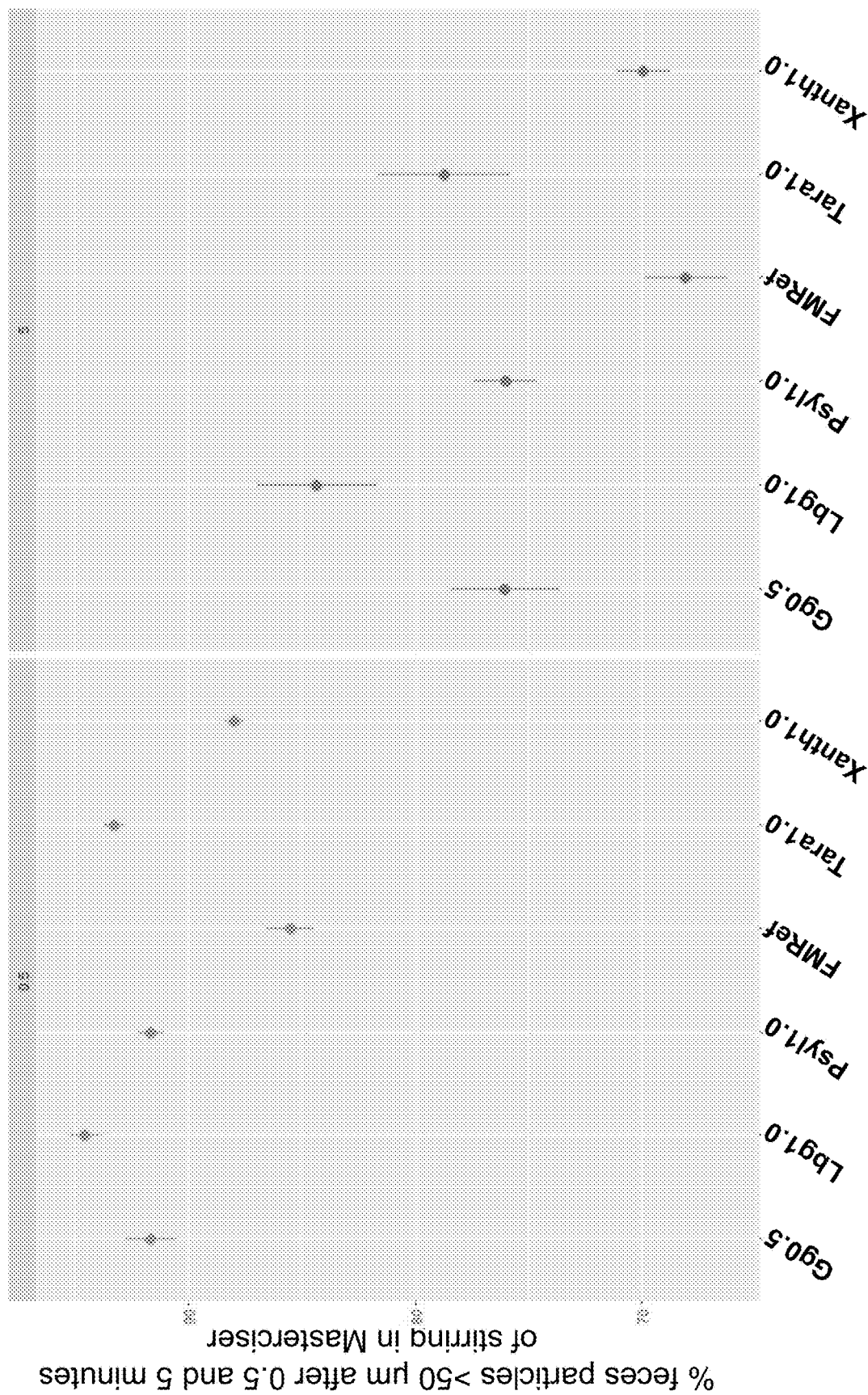
FIG. 1 shows percent of feces particles greater than 50 μm after 0.5 (left) and 5 (right) minutes of stirring in Mastersizer based on the fish feed formulations outlined in Example 1.

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that about 0 wt % to about 5 wt % of the composition is the material, or about 0 wt % to about 1 wt %, or about 5 wt % or less, or less than or equal to about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

Feed Compositions Including a Binding Agent

Various aspects of the present disclosure provide a composition including a binding agent. The composition is a fish feed, or a feed product for forming the fish feed. The feed product can be designed to be mixed with another composition, such as a base fish feed, or form the fish feed. The fish feed can be formulated for use in any suitable life stage of the fish, such as for use with fry, juvenile, smolt, adult, and/or spawning fish.

The fish may be a carnivorous fish. As used herein "carnivorous" refers to a fish family or species whose food, energy, and nutrient requirements, when in their native, wild habitat, may be derived solely from animal tissue or meat. In a fish farm, carnivorous fish may be fed vegetable based or omnivorous diets, however the term carnivorous applies to the fish's natural state in the wild. Carnivorous fish include, but are not limited to, salmonids, tunas and mackerels, eels, flatfish, amberjacks, striped bass sea bass and other bass, sea bream and other breams, codfish, barramundi, pompano, lumpfish, wrasse, wolf fish and the like.

As used herein, "salmonids" refers to a fish of the family Salmonidae. Salmonids include, but are not limited to, salmon, trout, char, freshwater whitefish, and graylings. The salmonid may be, but is not limited to, an Atlantic salmon (*Salmo salar*), a species of salmon native to the Pacific Ocean (*Oncorhynchus* sp.), Rainbow trout (*Oncorhynchus mykiss*), Coho salmon (*Oncorhynchus kisutch*), and the like.

As used herein, "binding agent" or "feces binder" are interchangeably and refer to an agent which, when included in a feed composition consumed by a fish, will increase the particle size and/or stability of feces produced and excreted by said fish. The binding agent may be a galactomannan polysaccharide, psyllium husk, xanthan gum, or combinations thereof. In general, the binding agent is a non-starch binding agent distinct from any starch-based binder included in a fish feed to stabilize the feed particles.

In some embodiments, the binding agent is or comprises a galactomannan polysaccharide. The galactomannan polysaccharide may have a mannose to galactose ratio of about 3:1, about 4:1, or about 5:1. The mannose to galactose ratio may be about 3-5:1, about 3-4:1, or about 4-5:1. In some embodiments, the mannose to galactose ratio is greater than 2:1, equal to greater than 3:1, equal to greater than 4:1, or equal to greater than 5:1. Suitable galactomannan polysaccharides include, but are not limited to, tara gum, locust bean gum, cassia gum, and combinations thereof. Guar gum has a ratio of mannose to galactose of about 2:1, and, if included in the fish feed, is included in addition to at least one of tara gum, locust ben gum, cassia gum, psyllium husk, and xanthan gum. Tara gum has a ratio of mannose to galactose of about 3:1. Locust bean gum has a ratio of mannose to galactose of about 4:1. Cassia gum has a ratio of mannose to galactose of about 5:1.

The binding agent can form any suitable portion of the fish feed. For example, the binding agent can be 0.1 wt % to 5 wt % of the fish feed, 0.2 wt % to 3 wt %, 0.5 wt % to 2 wt %, or 0.1 wt % or more, or less than, equal to, or greater than 0.1 wt %, 0.2 wt %, 0.3 wt %, 0.4 wt %, 0.5 wt %, 0.6 wt %, 0.7 wt %, 0.8 wt %, 0.9 wt %, 1.0 wt %, 1.1 wt %, 1.2 wt %, 1.3 wt %, 1.4 wt %, 1.5 wt %, 1.6 wt %, 1.7 wt %, 1.8 wt %, 1.9 wt %, 2.0 wt %, 2.2 wt %, 2.4 wt %, 2.6 wt %, 2.8 wt %, 3.0 wt %, 3.2 wt %, 3.4 wt %, 3.6 wt %, 3.8 wt %, 4.0 wt %, 4.2 wt %, 4.4 wt %, 4.6 wt %, 4.8 wt %, or 5 wt % or less of the fish feed.

The locust bean gum, tara gum, or cassia gum binding agent may be added to the feed as locust bean meal, tara meal, or cassia meal, respectively. The locust bean gum, tara gum, or cassia gum binding agent may be added to the feed as a crude locust bean product, a crude tara product, or a crude cassia product, respectively. The recited meals and crude products include the locust bean gum, tara gum, or cassia gum binding agent as well as protein, fat, and carbohydrates. Locust bean meal or crude product may be extracted from a locust bean seed (*Ceratonia siliqua*). Tara meal or crude product may be extracted from a tara seed (*Tara spinosa*). Cassia meal or crude product may be extracted from a cassia seed (*Cassia tora* or *Cassia obtusifolia*). If the locust bean gum, tara gum, or cassia gum is added in a composition of a meal or crude product, the meal or crude product is added to the feed at a concentration such that the feed includes between 0.1 wt % to 5 wt % of the locust bean, cassia, or tara gum, or any other suitable portion as described herein.

In some embodiments, the binding agent is or comprises xanthan gum. The xanthan gum may be present in the fish feed as purified xanthan gum or the xanthan gum may be added as part of a crude bacterial meal comprising the xanthan gum. The xanthan gum and crude bacterial meal comprising xanthan gum may be used interchangeably in the fish feed at a concentration such that the feed includes between 0.1 wt % and 5 wt % of the xanthan gum.

The binding agent may be combined with guar meal to form a combined binding agent. For example, a galactomannan polysaccharide, psyllium husk, or xanthan gum binding agent may be combined with 0.1% to 15%, 0.5% to 12%, 1.0% to 10.0%, or 2.0% to 8.0% guar meal, based on the total weight of the fish feed.

The fish feed can be a complete fish feed. A complete fish feed is a nutritionally adequate feed for fish that is compounded to be fed as the sole ration and can maintain life and/or promote growth and production without any additional substances being consumed except water. Complete feeds are compounded mixtures containing all the nutrients of concentrates plus various energy sources such as grains (starch), some fat, and the like. In addition, certain major vitamins and minerals may be added. A complete feed can include ingredients such as, but not limited to, fishmeal, poultry meal, plant meal, vegetable meal, corn meal, corn gluten meal, soy meal, soy protein concentrate, single cell protein, insect meal, algae meal, algae oil, krill meal, krill oil meat meal, blood meal, feather meal, starches, tapioca starch, wheat, wheat gluten, guar meal, guar protein concentrate peas, pea protein concentrate, pea starch, beans, faba beans, sunflower meal, vegetable oil, canola oil, poultry oil, rapeseed oil, fish oil, soy oil, linseed oil, camelina oil, lecithin, macro-minerals, minerals, vitamins, amino acids, pigment, astaxanthin, canthaxanthin and combinations thereof. One skilled in the art would appreciate that either a meal or a protein concentrate may be used in a feed formulation.

The total protein in the fish feed may be between 10 wt % and 70 wt %, between 15 wt % and 65 wt %, between 20 wt % and 60 wt %, or between 25 wt % and about 55 wt %. The total protein in the fish feed may be at least 10%, 15%, 20%, 25%, 30%, 35%, 38%, 40%, 42%, 44%, 46%, 48%, 50%, 52%, 55%, 60%, 65%, or at least 70% by weight. The total protein in the fish feed may be variable depending on the formulation, species, and intended use of the feed. One of skill in the art will recognize the various protein requirements of fish receiving the fish feed and can adjust the protein content accordingly.

The protein in the fish feed may be from any suitable source including, but not limited to, fishmeal, land-animal protein (e.g., poultry meal), plant-based protein (e.g., vegetable meal), or combinations thereof. The fish feed may include between 0% and 80%, between 10% and 80%, between 20% and 75%, between 30% and 70%, between 60% and 80%, or between 10% and 30%, or at least 10%, 20%, 30%, 40%, 50%, 60%, 70%, or 75% fishmeal. The fish feed may include between 0% and 80%, 10% and 80%, between 20% and 75%, between 30% and 70%, between 60% and 80%, or between 10% and 30%, or at least 10%, 20%, 30%, 40%, 50%, 60%, 70%, or 75% land-animal protein. The fish feed may include between 0% and 80%, between 10% and 80%, between 20% and 75%, between 30% and 70%, between 60% and 80%, or between 10% and 30%, or at least 10%, 20%, 30%, 40%, 50%, 60%, 70%, or 75% plant-based protein. Additionally, the fish feed may be free of any one or more fishmeal, land-animal protein, or plant-based protein.

Total fat (e.g., oil, fat, and/or lipids) in the fish feed may be between 5% and 50%, between 10% and 45%, between 15% and 40%, or between 20% and 35%. The total fat in the fish feed may be at least 5%, 10%, 15%, 20%, 25%, 30%, 35%, 40%, 45%, or at least 50%. The total fat in the fish feed may be variable depending on the formulation, species, and intended use of the fish feed. One of skill in the art will recognize the various fat requirements of fish receiving the fish feed and can adjust the fat content accordingly.

The fat in the fish feed may be from any suitable source, including, but not limited to, canola oil, poultry oil, rapeseed oil, fish oil, soy oil, linseed oil, camelina oil, palm oil, lecithin and combinations thereof.

The fish feed may additionally include astaxanthin. The fish feed may include between 0.01 and 100 mg astaxanthin/kg diet. The fish feed may include at least 0.01 mg, 0.1 mg, 0.2 mg, 0.5 mg, 1 mg, 5 mg, 10 mg, 20 mg, 30 mg, 40 mg, 50 mg, 60 mg, 70 mg, 80 mg, 90 mg, or at least 100 mg astaxanthin per kg diet. In some aspects, canthaxanthin may be used as an alternative to astaxanthin in similar concentration in the fish feed.

The moisture content of the fish feed may vary depending on the contents and preparation method of the feed. In general, the moisture content may be between 1% and 20%, between 2% and 18%, between 5% and 15%, or between 6% and 12%.

The fish feed may be a feed suitable for fish in any life stage and raised in water of any salinity. One skilled in the art would understand the requirements for fish at various life stages in water of varying salinity.

The fish feed may be an extruded, pressed, or particulate fish feed. The fish feed may be of any size appropriate for the fish being feed. For example, a fish feed for a small fish (e.g., less than 100 g) may have an average size between about 0.2 mm and about 4.5 mm in length and diameter (e.g., an average size of 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5 mm). A fish feed for a large fish (e.g., more than about 100 g) may have an average size between about 4.5 mm and about 12 mm in length and diameter (e.g., an average 4.5, 4.6, 4.7, 4.8, 4.9, 5.0, 5.1, 5.2, 5.3, 5.4, 5.5, 5.6, 5.7, 5.8, 5.9, 5.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0 mm). In general, a fish may be fed and consume fish feed for a particular size or smaller. For example, as demonstrated in the table below, a 1 g fish may be fed a 1.3 mm pellet or any smaller size pellet. A fish may be fed a feed that is at most 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 5.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 mm in length and diameter. One of skill in the art will recognize the various size requirements of fish receiving the fish feed and can adjust the feed size accordingly.

TABLE 1

Exemplary pellet sizes and fish size recommendations

| Atlantic Salmon fish size from (g) | Rainbow Trout fish size from (g) | Pellet mm |
| --- | --- | --- |
| 0.15 (first feeding) | 0.15 (first feeding | 0.6 |
| 0.4 | 0.4 | 0.9 |
| 1 | 1 | 1.3 |
| 5 | 5 | 1.7 |
| 15 | 15 | 2.2 |
| 40 | 40 | 3 |
| 80 | 80 | 4 |
| 200 | 250 | 4.9 |
| 500 | 600 | 7 |
| 1000 | 1500 | 9 |

All sizes have the same length/diameter

Methods

Various aspects of the present disclosure provide methods for feeding a fish. The method includes feeding a fish a fish feed including a binding agent as described herein. The method provides certain advantages to fish farming or fish rearing as compared to a corresponding method using a fish feed that does not include the binding agent. When fish are fed the fish feeds containing a binding agent as described herein, the method decreases suspended solids in the rearing water of the fish as compared to the suspended solids in rearing water of a fish feed without the binding agent. When fish are fed the fish feeds containing a binding agent as described herein, the method decreases undesired nutrients in water discharged from a fish farming or fish rearing system as compared to undesired nutrients in water discharged from an equivalent system in which fish are fed a feed lacking the binding agent. When fish are fed the fish feeds containing a binding agent as described herein, the method increases the amount of feces removed from a fish farming or fish rearing system by filtration or settling as compared to the amount of feces removed by equivalent methods from equivalent systems in which fish are fed a feed lacking the binding agent. When fish are fed the fish feeds containing a binding agent as described herein, the method increases mechanical strength, shear resistance, and/or size of feces particles produced by the fish relative to that of feces produced by fish fed an equivalent diet lacking the binding agent.

The method may include any suitable method for feeding a fish fed to a fish and may be used any fish farming or rearing system. The method may include feeding a fish in a recirculating aquaculture system, flow through system, partial water reuse system, in an open net pen farming system, semi closed pen system, closed pen system. The fish farming or rearing system may be a system of any salinity suitable for the fish being raise, for example, a freshwater, a brackish, or a saltwater system.

The method may include feeding fish at any life stage. For example, the method of feeding may include feeding fry, juvenile, smolt, adult, and/or spawning fish. The fish may also be fed the fish feed including the binding agent for any period of time and across life stages. For example, smolt fish may be fed the fish feed including the binding agent and the same fish may continue to receive a feed including the binding agent upon reaching and throughout adulthood.

The methods described can increase feces size from fish fed the fish feeds described herein. For example, the method can increase feces size at least 5%, at least 10%, at least 15%, or at least 20% as compared to feces size from fish fed an equivalent diet lacking the binding agent.

The methods described can increase filterability of feces produced by fish fed the fish feeds containing a binding agent as described herein. Filterability is calculated as the percentage of feces particles greater than 50 µm after 5 minutes of stirring 2500 rpm. For example, at least 70%, at least 75%, at least 80%, at least 85%, at least 90%, or at least 95% of the feces particles are greater than 50 µm after 5 minutes of stirring. An increase in the percentage of feces particles greater than 50 µm after 5 minutes of stirring at 2500 rpm also indicates an increase in mechanical strength of the feces and an increase in shear resistance. Suitable processes and equipment are known in the art for evaluating and quantifying filterability.

The methods described can decrease suspended solids in the rearing water of the fish as compared to the suspended solids in rearing water of a fish feed without the binding agent. For example, suspended solids in rearing water may be decreased at least 5%, at least 8%, at least 10%, at least 15%, at least 20%, or at least 30% relative to the suspended solids in rearing water of fish fed an equivalent feed lacking the binding agent.

The methods described can decrease undesired nutrients in water discharged from a fish farming or fish rearing system as compared to undesired nutrients in water discharged from an equivalent system in which fish are fed a feed lacking the binding agent. For example, undesired nutrients in water discharged from a fish farming or fish rearing system may be reduced by at least 5%, at least 8%, at least 10%, at least 15%, at least 20%, or at least 30% relative to undesired nutrients in water discharged from an equivalent system in which fish are fed a feed lacking the binding agent.

The method described can increase the amount of feces removed by filtration or settling from a fish farming or fish rearing system as compared to the amount of feces removed by equivalent methods from equivalent systems in which fish are fed a feed lacking the binding agent. For example, at least 5%, at least 10%, at least 20%, at least 25%, at least 30%, at least 40%, at least 50%, at least 60%, at least 70%, at least 75%, at least 80%, at least 85%, at least 90%, at least 95%, or at least 100% more feces may be removed by filtration or settling that would be removed if fish were fed an equivalent diet lacking the binding agent. The amount of feces removed by filtration or settling can be at least 2 times, 3 times, 4, times, 5 times, 6 times, 7 times, 8 times, 9 times, or at least 10 times greater than the amount removed if fish were fed an equivalent diet lacking the binding agent.

EXAMPLES

Example 1

The test feeds for this example are based on the reference diet base mix containing 53.5% protein and 21.9% fat. The detailed formulation of the reference diet base mix is given in Table 2 and the diet formulations with binding agents are outlined in Table 3. The analyzed trial feed compositions are given in Table 4. The extruded feeds have a pellet diameter of 4 mm.

TABLE 2

Reference Diet Base Mix ("FMRef")

| Ingredient | % diet (weight %) |
|---|---|
| Fishmeal | 71.90 |
| Wheat grain | 14.60 |
| Additives | 0.49 |
| Rapeseed oil | 6.51 |
| Fish oil | 6.51 |
| Total | 100 |

TABLE 3

Diet formulations with binding agents.

| | % diet (weight %) | | | | |
|---|---|---|---|---|---|
| | Gg0.5 | Tara1.0 | Lbg1.0 | Psyl1.0 | Xanth1.0 |
| Guar gum | 0.5 | | | | |
| Tara gum | | 1.00 | | | |
| Locust bean gum | | | 1.00 | | |
| Psyllium husk | | | | 1.00 | |
| Xanthan gum | | | | | 1.00 |
| Fishmeal | 71.54 | 71.19 | 71.19 | 71.19 | 71.19 |
| Wheat grain | 14.52 | 14.45 | 14.45 | 14.45 | 14.45 |
| Additives | 0.48 | 0.48 | 0.48 | 0.48 | 0.48 |
| Rapeseed oil | 6.48 | 6.44 | 6.44 | 6.44 | 6.44 |
| Fish oil | 6.48 | 6.44 | 6.44 | 6.44 | 6.44 |
| Total | 100.00 | 100.00 | 100.00 | 100.00 | 100.00 |

TABLE 4

Trial feed analyzed composition.

|  | FM ref | Gg0.5 | Tara1.0 | Lbg1.0 | Psyl1.0 | Xanth1.0 |
|---|---|---|---|---|---|---|
| Protein (%; Leco) | 53.5 | 52.6 | 53.2 | 53.7 | 52.8 | 51.9 |
| Fat (%; LfNMR) | 21.9 | 23.0 | 23.0 | 23.1 | 22.6 | 22.3 |
| Gross Energy (MJ/kg; Leco) | 21.9 | 22.1 | 22.2 | 22.1 | 21.8 | 21.8 |
| Yttrium (mg/kg; XRF) | 207.1 | 217.1 | 208.4 | 193.9 | 201.1 | 190.0 |
| Moisture (%) | 9.0 | 8.3 | 8.4 | 8.4 | 9.4 | 9.7 |

Atlantic salmon were stocked in four replicate freshwater tanks per diet with 90 fish per tank and were estimated to be about 285 g fish weight at the time of feces sampling. Water temperature averaged 11.8° C. during the feces sampling week. Fresh feces were collected from each tank over three separate days after at least one week of acclimation feeding on trial diets. Feces binding was measured as a percentage of particles greater than 50 μm after 5 minutes of stirring as determined using laser diffraction on a Malvern Mastersizer 3000. The feces binding measurement represents the feces particles that can be removed by mechanical filtration The Mastersizer stirs at 2500 rpm when measuring the sample with a preliminary stirring period to reach an obscuration target, which can be 5-15 seconds, before laser diffraction measurements are taken over a 5 min period. A decrease in particle size is observed and recorded over a duration of 0.5 to 5 min due to the mixing activity in the instrument. The machine evaluated feces particle diameter at 10 time points, but statistical comparison given for two timepoints at 0.5 and 5 min to show the range for the decrease in particle size over time as appropriate for this procedure.

FIG. 1 shows the percentage of feces particles greater than 50 μm after either 0.5 minutes (left) or 5 minutes (right) of stirring in the Mastersizer.

Feces was also collected for digestibility evaluation with feces and fish feeds also analyzed for the nutrient and indigestible marker (yttrium oxide was added to the feeds, 0.02%). Suitable methods for analyzing and quantifying digestibility are known and described in the art. See, for example, Smith R. R. (2009) Nutritional Energetics Chapter 1 in Fish Nutrition $2^{nd}$ ed, Halver J. E. (ed), Academic Press Inc. San Diego California, USA, p. 19. In general, protein digestibility of the guar gum, locust bean gum, xanthan gum and tara gum diets were like the base diet, whereas fat digestibility increased 1% compared to the base diet except for xanthan gum which had decreased fat digestibility (median values; n=4). Unexpectedly, the psyllium husk diet showed consistently higher protein, fat and dry matter digestibility. Tara gum, locust bean gum and xanthan gum gave decreased dry matter digestibility.

Example 2

The test feeds for this example are based on the reference diet base mix containing 55.8% protein and 20.1% fat. The detailed formulation of the reference diet base mix is given in Table 2 and diet formulations with binding agents in this Example are outlined in Table 5. The analyzed trial feed compositions are given in Table 6. The extruded feeds had a pellet diameter of 4 mm.

TABLE 5

Diet formulations with binding agents.

| | % of diet (weight %) | | | | |
|---|---|---|---|---|---|
| | Lbg 0.375 | Lbg 0.750 | Lbg 1.125 | Lbg 1.500 | Gg 0.500 |
| Locust bean gum | 0.375 | 0.750 | 1.125 | 1.500 | — |
| Guar gum | — | — | — | — | 0.500 |
| Fishmeal | 71.59 | 71.28 | 70.97 | 70.66 | 71.49 |
| Wheat grain | 14.53 | 14.47 | 14.41 | 14.34 | 14.51 |
| Additives | 0.48 | 0.48 | 0.48 | 0.48 | 0.48 |
| Rapeseed oil | 6.51 | 6.51 | 6.51 | 6.51 | 6.51 |
| Fish oil | 6.51 | 6.51 | 6.51 | 6.51 | 6.51 |
| Total | 100.00 | 100.00 | 100.00 | 100.00 | 100.00 |

TABLE 6

Trial feed analyzed composition.

| | FMRef | Lbg0.375 | Lbg0.750 | Lbg1.125 | Lbg1.500 | Gg0.500 |
|---|---|---|---|---|---|---|
| Protein (%; Leco) | 55.8 | 54.3 | 54.3 | 53.7 | 54.0 | 54.1 |
| Fat (%; LfNMR) | 20.1 | 19.8 | 19.8 | 19.8 | 19.9 | 19.9 |
| Gross Energy (MJ/kg; Leco) | 21.5 | 21.3 | 21.2 | 21.3 | 21.2 | 21.3 |
| Yttrium (mg/kg; XRF) | 161.8 | 162.8 | 165.5 | 152.5 | 158.1 | 152.1 |
| Moisture (%) | 6.1 | 7.2 | 7.7 | 7.8 | 8.2 | 8.5 |

Atlantic salmon were stocked in four replicate freshwater tanks per diet with 70 fish per tank and were estimated to be about 112 g fish weight at the time of feces sampling. Water temperature averaged 13.5° C. during the feces sampling week. Fresh feces were collected from each tank over three separate days after at least one week of acclimation feeding on trial diets. Feces binding was measured as a percentage of particles greater than 50 μm after 5 minutes of stirring as determined using laser diffraction on a Mastersizer. This feces binding measurement represents the feces particles that can be removed by mechanical filtration. The particle size and digestibility analysis methods are the same as those outlined in Example 1.

Figure 2:
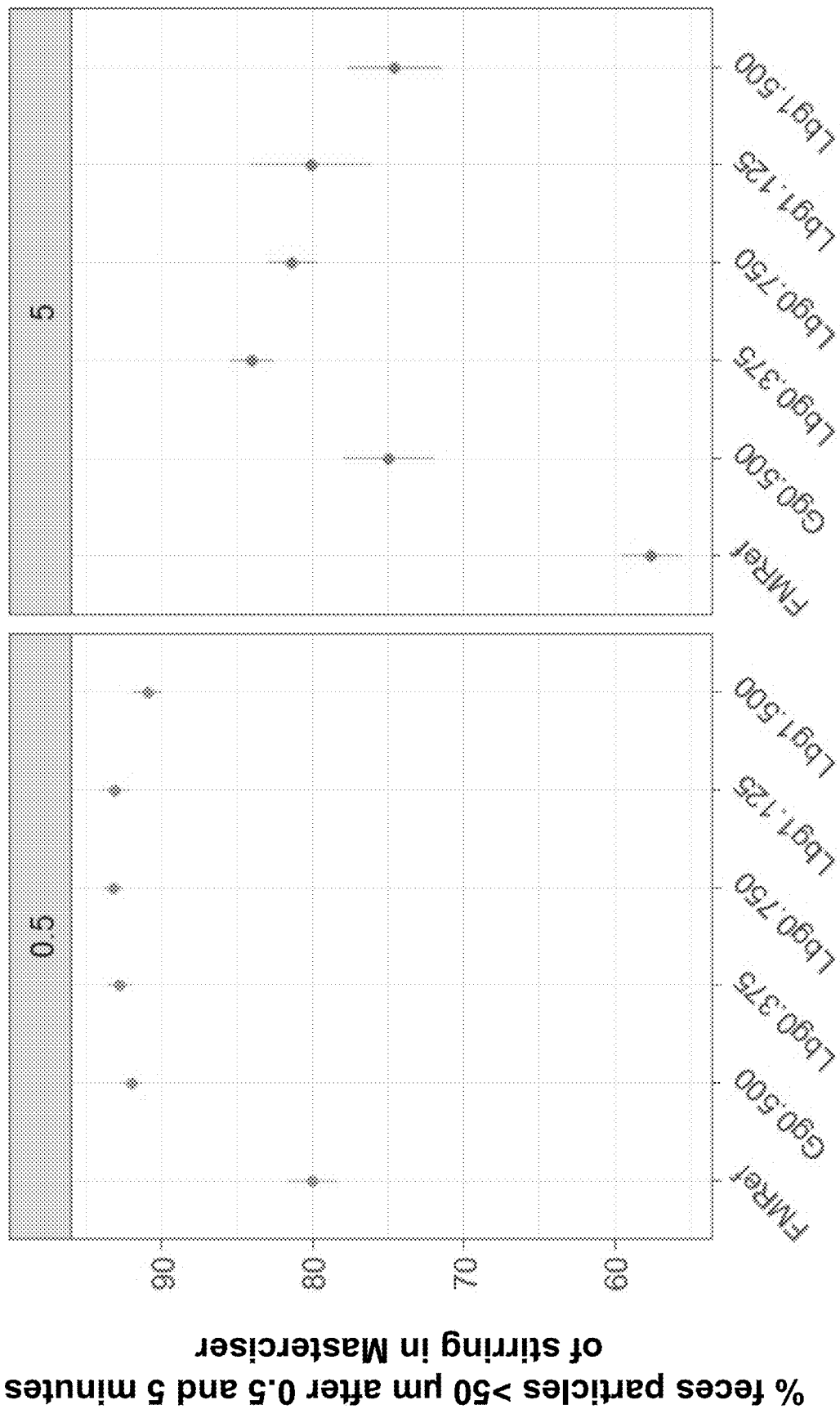
FIG. 2 shows percent of feces particles greater than 50 μm after 0.5 (left) and 5 (right) minutes of stirring in Mastersizer based on the fish feed formulations outline in Example 2.

FIG. 2 shows the percent of feces particles greater than 50 μm after 0.5 minutes (left) and 5 minutes (right) of stirring at 2500 rpm. All the trial diets showed significant increases in feces particle size after 5 minutes as compared to the base diet.

Protein and dry matter digestibility were similar across the Gg0.5, Lbg0.375 and Lbg 0.75 diets evaluated for digestibility (not enough feces to analyze for some tanks), while the 0.375% locust bean gum diet showed decreased fat digestibility≤1% median difference to the other two diets (n=4).

Example 3

This example uses a 2×2 with centerpoint experimental design based on including the factors of locust bean gum and an ingredient mix containing land animal and plant-based proteins to evaluate the effects on feces particle size and digestibility. The diets used in this example ranged from 52.7-55.8% protein and 19.6-21.3% fat. The formulations of the diets used in this example are outlined in Table 7. The analyzed trial feed compositions are given in Table 8. The extruded feeds had a pellet diameter of 4 mm. The FMRef diet is the same diet used in Examples 1 and 2. The FMLbg diet replaced a portion of the FMRef meal mix with 1.15% locust bean gum resulting in a diet with 1.0% locust bean gum. For the Test diet, an ingredient mix containing land animal proteins was added at 51.9% of diet replacing fish meal in the FMRef diet to give 20% FM of diet in the Test diet. The TestLbg diet replaced a portion of 1 the Test meal mix with 1.15% locust bean gum resulting in a diet with 1.0 locust bean gum. The Centerpoint diet is an average of the previous four diets providing a center point formulation. The Test v2 diet is a rework diet based on the Test diet. An extruded pellet of the Test diet that was reground and used to replace a portion of the Test meal mix.

TABLE 7

Diet formulations

| Ingredient (% diet) | FMRef | FMLbg | Test | TestLbg | Centerpoint | Test v2 |
|---|---|---|---|---|---|---|
| Fishmeal | 71.9 | 71.1 | 20.0 | 19.8 | 45.7 | 20.0 |
| Land animal protein | 0.0 | 0.0 | 39.6 | 39.1 | 19.7 | 39.6 |
| Vegetable protein | 0.0 | 0.0 | 12.3 | 12.2 | 6.1 | 12.3 |
| Wheat grain | 14.6 | 14.4 | 14.6 | 14.4 | 14.5 | 14.6 |
| Additives | 0.5 | 0.5 | 0.5 | 0.5 | 0.5 | 0.5 |
| Locust bean gum | 0.0 | 1.0 | 0.0 | 1.0 | 0.5 | 0.0 |
| Rapeseed oil | 6.5 | 6.5 | 6.5 | 6.5 | 6.5 | 6.5 |
| Fish oil | 6.5 | 6.5 | 6.5 | 6.5 | 6.5 | 6.5 |
| Total | 100.0 | 100.0 | 100.0 | 100.0 | 100.0 | 100.0 |

TABLE 8

Trial feed analyzed composition.

| | FMRef | FMLbg | Test | TestLbg | Centerpoint | TestV2 |
|---|---|---|---|---|---|---|
| Protein (%; Leco) | 55.8 | 53.1 | 53.7 | 52.7 | 53.1 | 54.1 |
| Fat (%; LfNMR) | 20.1 | 19.6 | 21.3 | 21.2 | 20.2 | 21.2 |
| Gross Energy (MJ/kg; Leco) | 21.5 | 21.1 | 22.4 | 22.4 | 21.7 | 22.6 |
| Yttrium (mg/kg; XRF) | 161.8 | 157.8 | 146.5 | 155.7 | 146.1 | 177.2 |
| Moisture (%) | 6.1 | 9.6 | 9.7 | 9.0 | 9.3 | 8.1 |

Atlantic salmon were stocked in four replicate freshwater tanks per diet with 70 fish per tank and were estimated to be about 189 g fish weight at the time of feces sampling. Water temperature averaged 13.6° C. during the feces sampling week. Fresh feces were collected from each tank over three separate days after at least one week of acclimation feeding on trial diets. Feces binding was measured as a percentage of particles greater than 50 µm after 5 minutes of stirring at 2500 rpm as determined using laser diffraction on a Mastersizer. This feces binding measurement represents the feces particles that can be removed by mechanical filtration. The particle size and digestibility analysis methods are the same as those outlined in Example 1.

Figure 3:
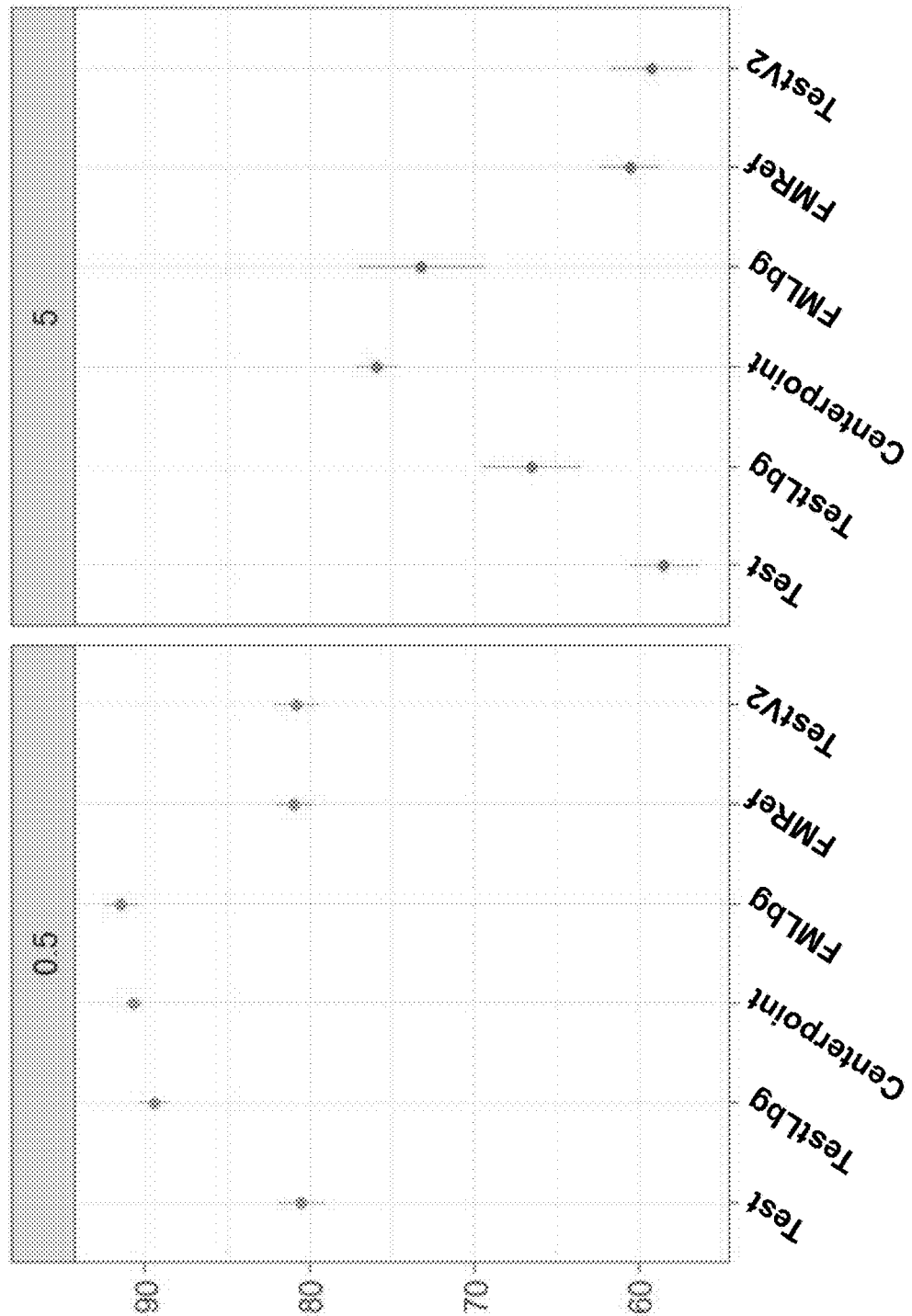
FIG. 3 shows percent of feces particles greater than 50 μm after 0.5 (left) and 5 (right) minutes of stirring in Mastersizer based on the fish feed formulations outlined in Example 3.

FIG. 3 shows percentage of feces particles greater than 50 µm after 0.5 minutes (left) and 5 minutes (right) of stirring. The three diets containing locust bean gum, FMLbg, TestLbg, and Centerpoint, showed a significant increase in particle size after both 0.5 and 5 minutes of stirring at 2500 rpm as compared to the control diets, FMRef and Test.

In general, the inclusion of locust bean gum at 1% of the trial diets reduced protein, fat, and dry matter digestibility, except for fat digestibility of the FMLbg diet. The CntrPt, which was an average of the FMRef, FMLbg, Test, and TestLbg diets and included 0.5% locust bean gum had intermediate digestibility.

Example 4

Extruded feeds were made at CIC Dirdal pilot plant with binder additives directly replacing the meal mix of the LtFmRef base diet with locust bean gum added in a dose response to compare against guar meal and LtFmRef diet for effect on feces particle size and digestibility for salmon in seawater. The test feeds for this example are based on the reference diet base mix containing 43.7% protein and 30.6% fat. The detailed formulation of the reference diet base mix is given in Table 9 and the diet formulations with binding agents in this Example are outlined in Table 10. The analyzed trial feed compositions are given in Table 11. The extruded feeds had a pellet diameter of 4 mm. The embodiments described in this example demonstrate that locust bean gum binding agents can be used in saltwater fish feeds in addition to the freshwater fish feeds demonstrated in Examples 1-3.

TABLE 9

Reference diet base mix ("LtFmRef")

| Ingredient | % of diet |
|---|---|
| Fish protein | 42.0 |
| Vegetable protein | 15.0 |
| Wheat grain | 14.6 |
| Additives | 1.87 |
| Fish oil | 26.5 |
| Total | 100.0 |

TABLE 10

Diet formulations with binding agents.

| Trial Diets | 0.2 Lbg | 0.4 Lbg | 0.6 Lbg | 0.8 Lbg | Gg 0.500 |
|---|---|---|---|---|---|
| Locust bean gum | 0.20 | 0.40 | 0.60 | 0.80 | |
| Guar gum | | | | | 0.50 |
| Fish protein | 41.88 | 41.77 | 41.65 | 41.54 | 41.71 |
| Vegetable protein | 14.96 | 14.92 | 14.88 | 14.84 | 14.90 |
| Wheat grain | 14.59 | 14.55 | 14.51 | 14.47 | 14.53 |
| Additives | 1.87 | 1.86 | 1.86 | 1.85 | 1.86 |
| Fish oil | 26.50 | 26.50 | 26.50 | 26.50 | 26.50 |
| Total | 100.00 | 100.00 | 100.00 | 100.00 | 100.00 |

TABLE 11

Trial feed analyzed composition.

| | LtFMRef | Lbg0.2 | Lbg0.4 | Lbg0.6 | Lbg0.8 | Gg0.5 |
|---|---|---|---|---|---|---|
| Protein (%; Leco) | 43.7 | 42.4 | 41.7 | 42.0 | 41.8 | 41.4 |
| Fat (%; LfNMR) | 30.6 | 32.7 | 32.7 | 32.2 | 33.1 | 30.7 |
| Yttrium (mg/kg; XRF) | 146 | 138 | 141 | 142 | 139 | 138 |
| Moisture (%) | 6.9 | 6.7 | 6.7 | 6.8 | 7.0 | 7.9 |

Atlantic salmon were stocked in four replicate saltwater tanks per diet with 45 fish per tank and were an estimated to be about 1.0 kg fish weight at time of feces sampling. Fresh feces were collected from each tank over three separate days after at least one week of acclimation on experimental feeds. Feces binding was measured as a percentage of particles greater than 50 μm after 5 minutes of stirring at 2500 rpm as determined using laser diffraction on a Mastersizer. The feces binding measurement of 50 μm represents the feces particles that can be removed by mechanical filtration. The particle size and digestibility analysis methods are the same as those outlined in Example 1.

Figure 4:
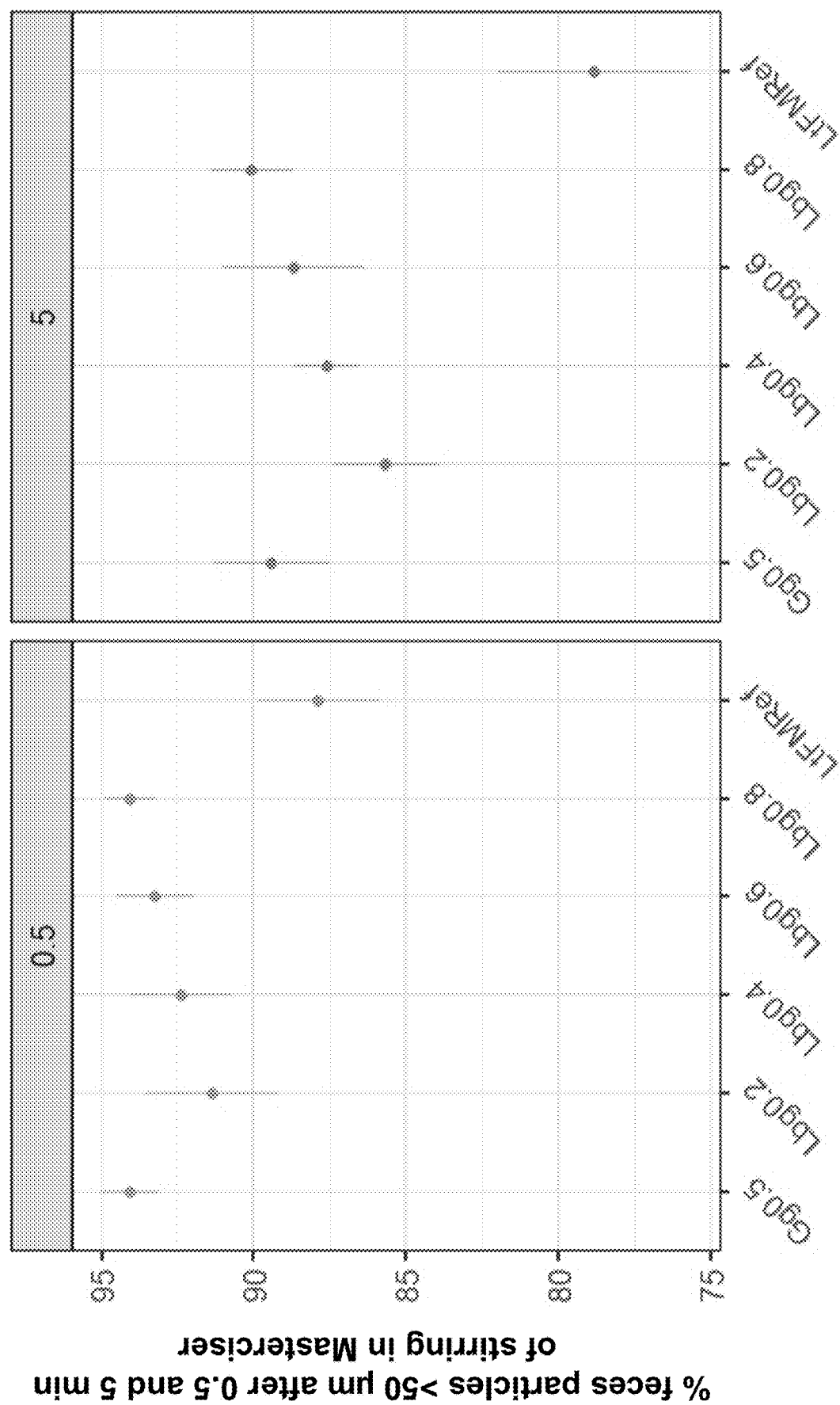
FIG. 4 shows percent of feces particles greater than 50 μm after 0.5 (left) and 5 (right) minutes of stirring in Mastersizer based on the fish feed formulations outlined in Example 4.

FIG. 4 shows percentage of feces particles greater than 50 μm after 0.5 minutes (left) and 5 minutes (right) of stirring. In general, the inclusion of guar gum or locust bean gum in the diet significantly increased feces particle size compared to the LtFMRef control diet.

Protein digestibility of the test diets is consistent with the LtFMRef control diet. Fat digestibility in the guar gum and locust bean gum diets decreased compared to the reference diet. While the 0.2 and 0.4 locust bean gum diets showed dry matter digestibility consistent with the reference diet, the guar gum, 0.6 locust bean gum, and 0.8 locust bean gum diets showed decreased dry matter digestibility.

Example 5

The test feeds for this example are based on the reference diet base mix containing 53.3% protein and 20.0% fat. The detailed formulations and analyzed composition of the diets used in this example are outlined in Table 12. The extruded feeds had a pellet diameter of 1.5 mm. The embodiments described in this example demonstrate the growth effects of locust bean gum diets on small freshwater salmon.

TABLE 12

| Ingredient (% diet) | Reference | LBG |
|---|---|---|
| Fishmeal | 27.5 | 27.6 |
| Plant meals | 56.6 | 55.8 |
| Additives | 3.1 | 3.1 |
| Fish oil | 6.4 | 6.4 |
| Rapeseed oil | 6.4 | 6.4 |
| Locust bean gum | | 0.75 |
| Total | 100.0 | 100.0 |
| Diet composition | | |
| Protein (% diet; NIR)* | 53.3 | 53.7 |
| Fat (% diet; LF NMR) | 20.0 | 20.1 |
| Moisture (% diet; NIR) | 5.8 | 5.5 |

Figure 5:
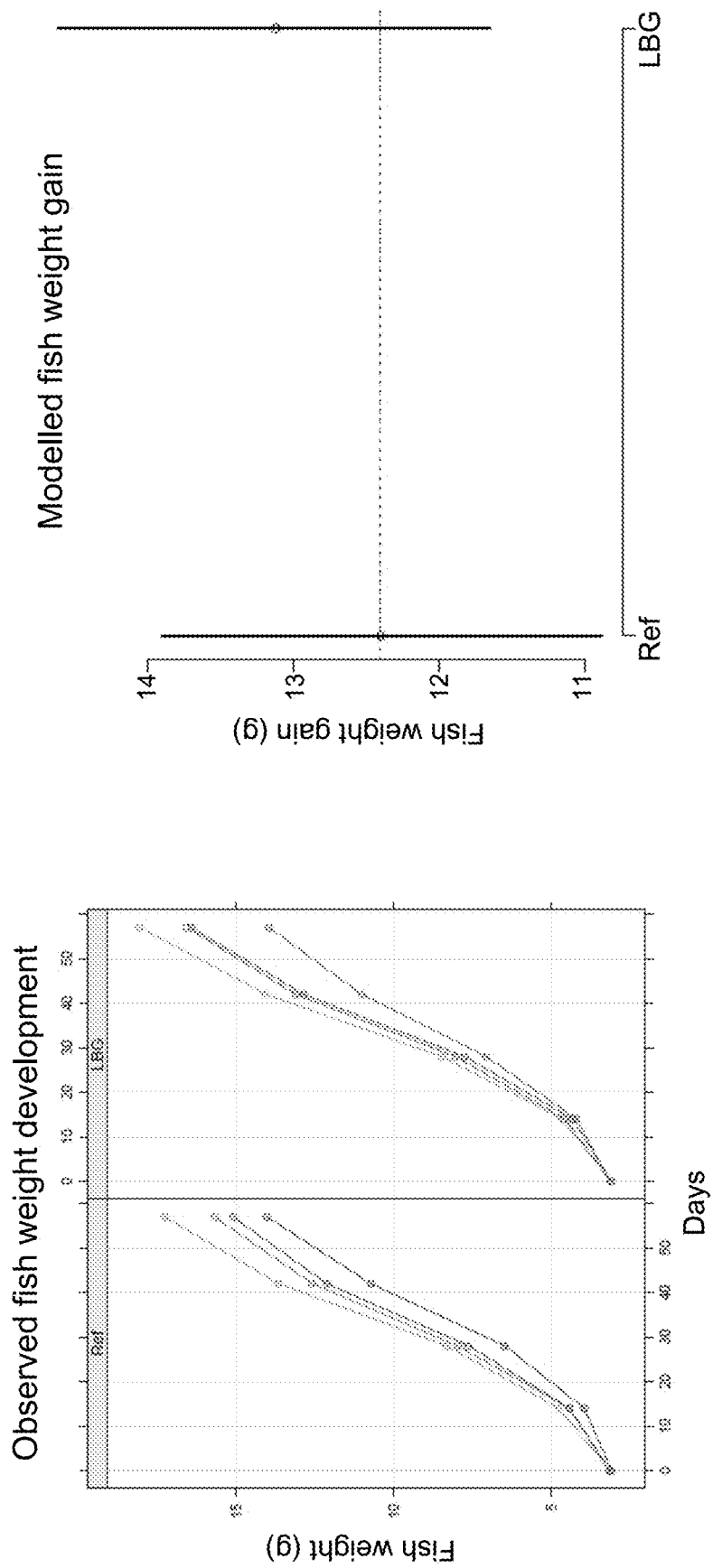
FIG. 5 shows observed (left) and modelled (right) fish weight development when fed either the Reference or LBG diet as outlined in Example 5.
Figure 6:
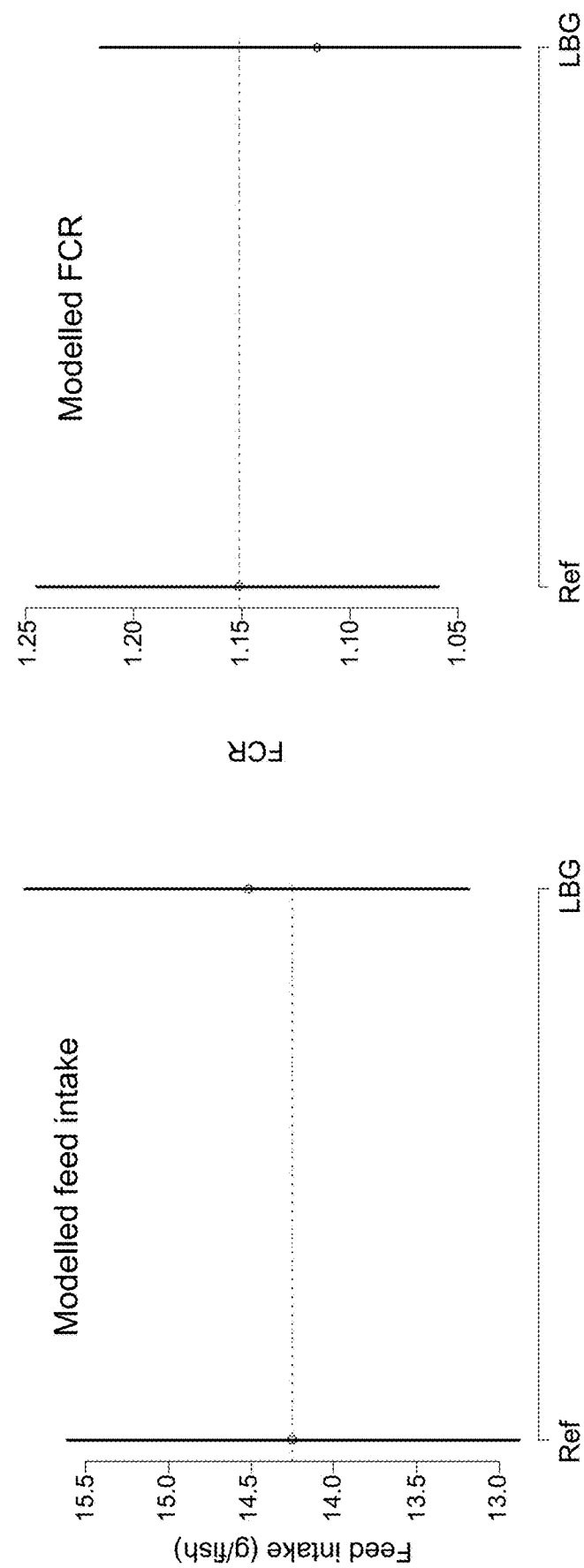
FIG. 6 shows modelled feed intake (left) and feed conversion ratio (FCR) (right) of fish fed wither the Reference or 0.75% LBG diet as outlined in Example 5.

Small Atlantic salmon were stocked in four replicate freshwater tanks per diet (n=100 fish per tank, mean weight=3.1 g) and growth was monitored over 8 weeks. At the end of the 8 weeks the overall average weight was 15.9 g. The temperature of the tanks averaged 12.9° C. (10.1-14.1° C. range) with decreased temperature the last 18 days of the trial due to maintenance work. Low mortalities were observed over the course of the trial, with no more than one mortality per tank. In general, similar growth was observed for salmon fed the 0.75% locust bean gum diet as compared to the reference diet. (See FIG. 5) Likewise, similar feed intake and feed conversion ratio (FCR) were also observed. (See FIG. 6) In general, the FCR reflects the feed to weight gain conversion between diets at the same level of energy. For example, an FCR of 1 indicates that 1 g of feed becomes 1 g of fish and an FCR of 2 indicates 2 g of feed becomes 1 g of fish, etc.

Example 6

The test feeds for this example are based on the reference diet base mix containing 53.3% protein and 19.5% fat. The detailed formulations of the diets used in this example are outlined in Tables 13 and 14. The extruded feeds had a pellet diameter of 1.3 mm. The embodiments described in this example demonstrate the dose response on growth effects of locust bean gum, guar gum, psyllium husk, and tara gum diets fed to small freshwater salmon.

Figure 7:
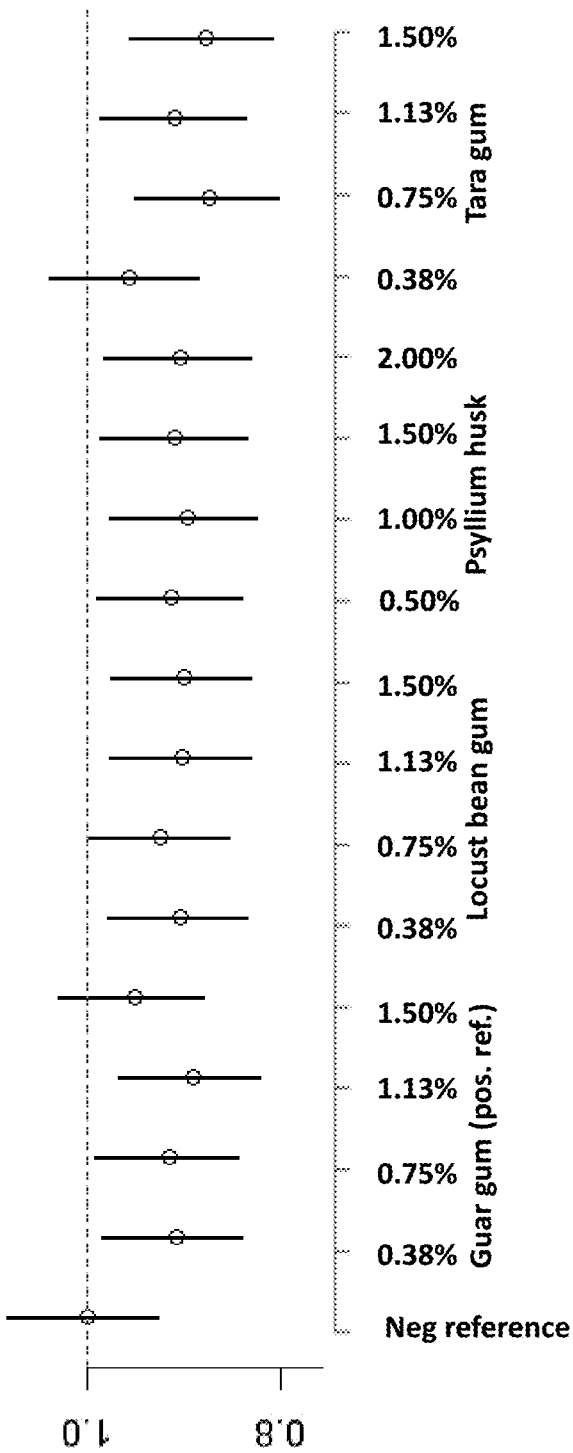
FIG. 7 shows freshwater salmon growth in salmon fed the diets outline in Example 6 relative to growth observed in salmon fed the reference diet. Salmon growth is measured as an overall tank average.

Small Atlantic salmon were stocked in four replicate freshwater tanks per diet (n=100 fish per tank, fish grew from 1.7 to 9.6 g; overall tank average) and growth was monitored over 54 d. Water temperature averaged 13.2° C. (12.3-13.7° C. range). Note there was a feeding error but only for 2 out of 54 d with trial feeds assigned to wrong tanks. At the end of the 8 weeks the overall average weight was 9.6 g. The data shows reduced growth in fish fed the diets including a binding agent versus the Ref diet, however it was unexpected that these different feces binding agents would significantly reduce growth especially at the lowest diet inclusion levels (except for tara) with no clear dose effect at higher inclusion if containing a negative growth factor (See FIG. 7). There was also no negative effect on small freshwater salmon growth in a later trial with similar setup that evaluated LBG at 0.75% of diet level (See FIG. 5) than the lower 0.38% or same 0.75% LBG of diet levels observed in this example which gave reduced growth.

TABLE 13

| Ingredient (% diet) | Ref | 0.38% GG | 0.75% GG | 1.13% GG | 1.50% GG | 0.38% LBG | 0.75% LBG | 1.13% LBG | 1.50% LBG |
|---|---|---|---|---|---|---|---|---|---|
| LT-Fishmeal | 38.7 | 39.8 | 40.8 | 41.9 | 42.9 | 39.8 | 40.8 | 41.9 | 42.9 |
| Vegetable protein | 36.7 | 35.4 | 34.2 | 32.9 | 31.6 | 35.4 | 34.2 | 32.9 | 31.6 |
| Tapioca | 8.2 | 8.2 | 8.2 | 8.2 | 8.2 | 8.2 | 8.2 | 8.2 | 8.2 |
| Additives | 4.0 | 3.9 | 3.8 | 3.8 | 3.7 | 3.9 | 3.8 | 3.8 | 3.7 |
| Fish oil | 6.2 | 6.1 | 6.1 | 6.1 | 6.0 | 6.1 | 6.1 | 6.1 | 6.0 |
| Rapeseed oil | 6.2 | 6.1 | 6.1 | 6.1 | 6.0 | 6.1 | 6.1 | 6.1 | 6.0 |
| Guar gum | | 0.375 | 0.750 | 1.125 | 1.500 | | | | |
| Locust bean gum | | | | | | 0.375 | 0.750 | 1.125 | 1.500 |
| Psyllium husk | | | | | | | | | |
| Tara gum | | | | | | | | | |
| Total | 100.0 | 100.0 | 100.0 | 100.0 | 100.0 | 100.0 | 100.0 | 100.0 | 100.0 |

| Ingredient (% diet) | 0.50% Psyl | 1.00% Psyl | 1.50% Psyl | 2.00% Psyl | 0.38% Tr | 0.75% Tr | 1.13% Tr | 1.50% Tr |
|---|---|---|---|---|---|---|---|---|
| LT-Fishmeal | 40.1 | 41.5 | 42.9 | 44.4 | 39.8 | 40.8 | 41.9 | 42.9 |
| Vegetable protein | 35.0 | 33.3 | 31.6 | 29.9 | 35.4 | 34.2 | 32.9 | 31.6 |
| Tapioca | 8.2 | 8.2 | 8.2 | 8.3 | 8.2 | 8.2 | 8.2 | 8.2 |
| Additives | 3.9 | 3.8 | 3.7 | 3.6 | 3.9 | 3.8 | 3.8 | 3.7 |
| Fish oil | 6.1 | 6.1 | 6.0 | 6.0 | 6.1 | 6.1 | 6.1 | 6.0 |
| Rapeseed oil | 6.1 | 6.1 | 6.0 | 6.0 | 6.1 | 6.1 | 6.1 | 6.0 |
| Guar gum | | | | | | | | |
| Locust bean gum | | | | | | | | |
| Psyllium husk | 0.500 | 1.000 | 1.500 | 2.000 | | | | |
| Tara gum | | | | | 0.375 | 0.750 | 1.125 | 1.500 |
| Total | 100.0 | 100.0 | 100.0 | 100.0 | 100.0 | 100.0 | 100.0 | 100.0 |

TABLE 14

| Ingredient | Ref | 0.38% GG | 0.75% GG | 1.13% GG | 1.50% GG | 038% LBG | 075% LBG | 1.13% LBG | 1.50% LBG |
|---|---|---|---|---|---|---|---|---|---|
| Protein (%; Dumas) | 53.3 | 53.4 | 52.8 | 52.6 | 51.1 | 53.9 | 54.5 | 53.5 | 52.4 |
| Fat (%; LF-NMR) | 19.5 | 19.2 | 19.1 | 19.4 | 19.6 | 19.2 | 19.2 | 19.0 | 19.2 |
| Moisture (%) | 8.0 | 8.4 | 10.6 | 9.7 | 11.1 | 8.4 | 6.6 | 8.2 | 9.3 |
| Energy (MJ/kg; Leco) | 21.7 | 21.6 | 21.5 | 21.5 | 21.3 | 21.8 | 22.1 | 21.7 | 21.6 |
| Water stability (%) | 70 | 69 | 71 | 72 | 74 | 74 | 76 | 72 | 69 |
| Turbidity | 767 | 1047 | 576 | 445 | 451 | 580 | 374 | 387 | 349 |
| Viscosity (RVA) | 1296 | 1934 | 2256 | 2778 | 2814 | 2461 | 2671 | 3094 | 3493 |

| Ingredient | 0.50% Psyl | 1.00% Psyl | 1.50% Psyl | 2.00% Psyl | 0.38% Tr | 0.75% Tr | 1.13% Tr | 1.50% Tr |
|---|---|---|---|---|---|---|---|---|
| Protein (%; Dumas) | 53.3 | 53.0 | 52.6 | 53.0 | 52.8 | 52.3 | 51.7 | 52.2 |
| Fat (%; LF-NMR) | 19.2 | 19.3 | 19.2 | 19.0 | 19.4 | 19.2 | 20.4 | 19.0 |
| Moisture (%) | 8.5 | 8.4 | 9.1 | 9.0 | 8.3 | 9.0 | 9.7 | 10.0 |
| Energy (MJ/kg; Leco) | 21.6 | 21.7 | 21.5 | 21.7 | 21.5 | 21.5 | 21.6 | 21.5 |
| Water stability (%) | 71 | 64 | 69 | 66 | 75 | 74 | 76 | 75 |
| Turbidity | 489 | 972 | 624 | 1124 | 273 | 388 | 253 | 347 |
| Viscosity (RVA) | 2373 | 2905 | 3668 | 5008 | 2097 | 2399 | 2851 | 3625 |

Example 7

Methods

Figure 8:
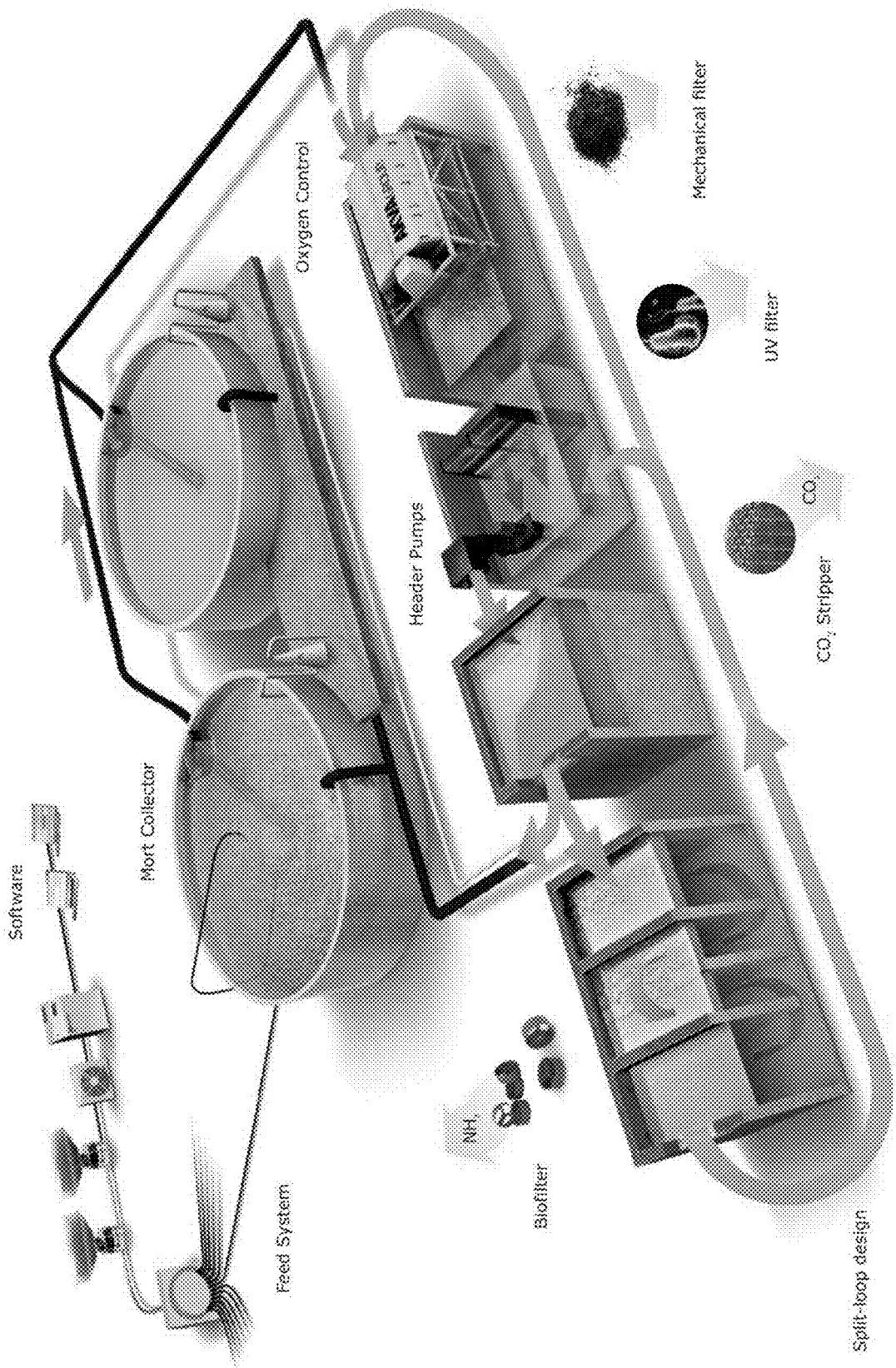
FIG. 8 shows a schematic of a RAS.
Figures 9A, 9B, 9C, 9D:
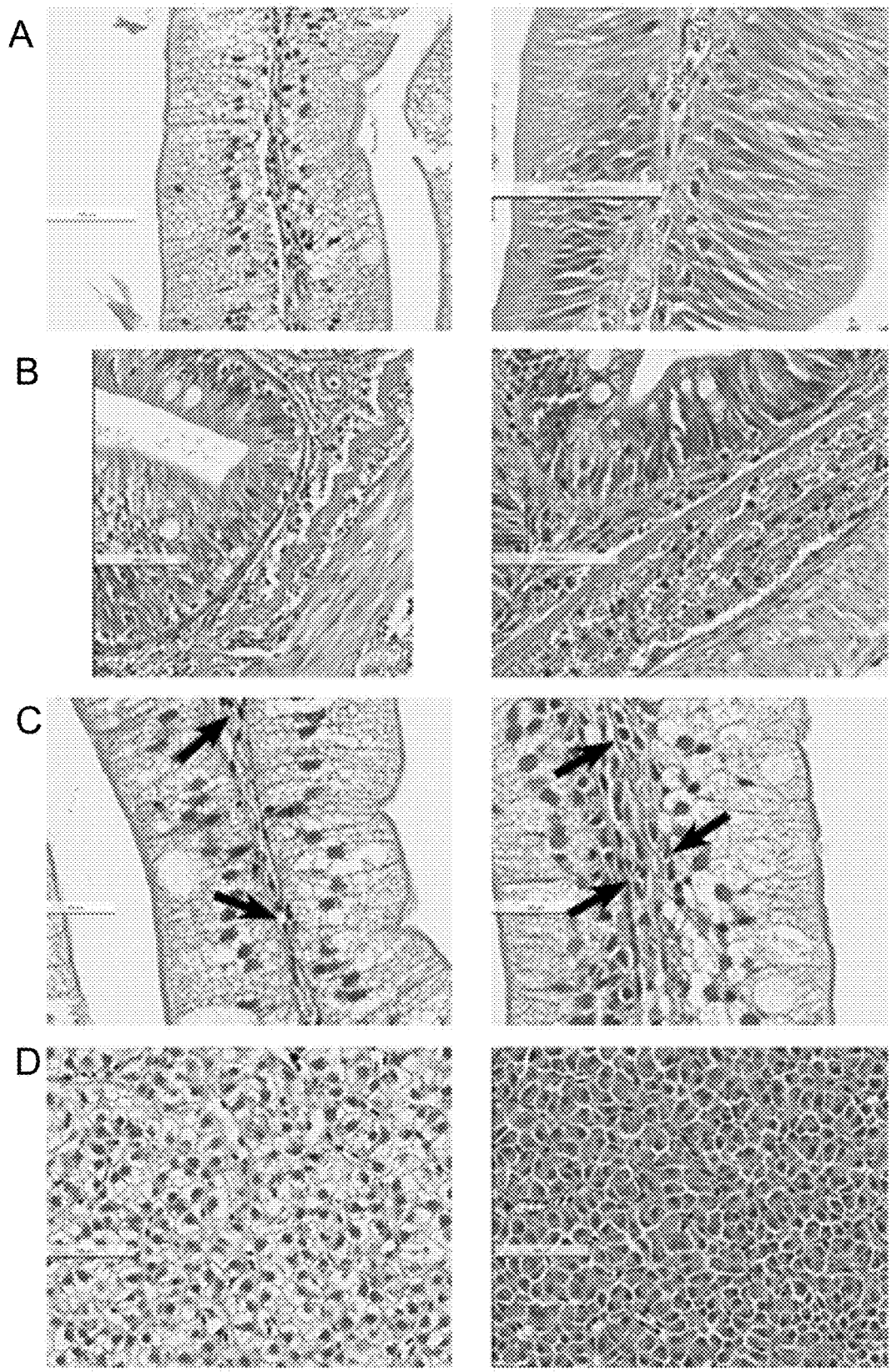
FIGS. 9A-9B show histopathological evaluation of distal intestine, pyloric ceca, and liver tissue samples.
(FIG. 9C) Scattered mononuclear cells in lamina propria (arrows), score of 1 (left) and 3 (right)
(FIG. 9D) Lipid and glycogen vacuolation expanding hepatocytes, score of 1 (left); absence of lipid and glycogen vacuolation presence, score of 5 (right).

Four experimental Atlantic salmon diet formulations (Table 15) were evaluated using a 2×2 factorial design where diets: i) contained or lacked locust bean gum and ii) were primarily formulated with fishmeal (FM) or land animal proteins (LAP) (Table 10). A key focus of this example was to evaluate how these formulations affected stability of fish fecal matter and related solids concentrations in the fish culture water, which are important criteria for recirculating aquaculture system (RAS) compatibility. Each diet was formulated with 42% protein and 30% fat, and a 10.5 mm pellet size was fed throughout the six-month study. Twelve identical partial reuse aquaculture systems (PRAS; FIG. 8) were used as experimental units of replication, three PRAS per diet treatment (n=3).

TABLE 15

2 × 2 factorial experimental design with four diet formulations with or without locust bean gum and with fishmeal or land animal proteins.

| Diet Label | Locust bean gum | Primary protein source | Number of experimental units |
|---|---|---|---|
| LAP | No | Land animal | 3 |
| FM | No | Fishmeal | 3 |
| B-LAP | Yes | Land animal | 3 |
| B-FM | Yes | Fishmeal | 3 |

Fish culture systems: Each PRAS recirculated 374±5 L/min (99±1 gpm) of freshwater through a 5 m³ dual drain culture tank, a gas conditioning column, and a low head oxygenator (FIG. 8). A continuous makeup water flow of 42.4±0.3 L/min (11.2±0.1 gpm) was added to each fish tank to replace water removed through the bottom center drain. This water exchange strategy resulted in a ratio of 89% water reuse and 11% water replacement.

Atlantic Salmon: Mixed-sex diploid Atlantic salmon were received as eyed eggs from Stofnfiskur ( Hafnarfjörður, Iceland) and hatched onsite in a Heath-tray-style recirculation system. Alevins were stocked in a flow-through system where they remained for eight months. When the fish reached approximately 50 g they were transferred to an adjacent partial reuse system described in Summerfelt et al. (2004). At a mean weight of approximately 75 g the fish were switched from constant 24-h lighting to a 12:12 light/dark photoperiod regimen to simulate winter and to instigate first-year smoltification. Following the winter photoperiod, fish were returned to 24-h lighting. Approximately ten weeks before the study, fish from this population (~1.4 kg mean weight) were randomly counted into twelve replicate PRAS. To begin the study, each tank contained 157 fish with a mean weight of 1.771±0.020 kg resulting in an average biomass density of approximately 56 kg/m3. Mortalities were removed and recorded daily to assess cumulative survival. Length and weight measurements of a random sample of 40 fish per PRAS were collected for baseline sampling. Sample number was increased to 45 fish per tank during subsequent sampling events to account for expanding standard deviation fish weights. Ultimately, 28-30% of fish in each PRAS were sampled during each size assessment.

Thermal growth coefficient (TGC), feed conversion ratio (FCR), and fish survival (%) were calculated using the following formula. Fish removed for histopathology and proximate compositional analysis were not included in the cumulative mortality count.

$$TGC = \frac{(\sqrt[3]{\text{End Weight}} - \sqrt[3]{\text{Initial Weight}})}{((\text{Days Between} * \text{Avg. Temp.}) * 1000} \text{ where}$$

weight is in grams and temperature in ° C $$FCR = \frac{\text{Cumulative Feed Delivered}}{\text{Fish Biomass Gain}}$$

$$\text{Survival \%} = \left(\frac{\text{Initial Number of Fish} - \text{Cumulative Mortalities}}{\text{Initial Number of Fish}}\right) * 100$$

Fish health: Fish health was assessed through histopathological evaluation of tissues collected from the distal intestine, pyloric ceca, and liver of five fish per PRAS (FIGS. 9A-9D). Fish remained on feed leading up to each sampling event to avoid a potential healing response related to cessation of feeding. Fish used for sampling were euthanized with a lethal dose of tricaine methanesulfonate (MS-222). Tissues were collected i) at the beginning of the study while all fish were fed the same base diet (Time 0), ii) approximately two weeks after start-feeding of experimental diets (Time 1), iii) four weeks into the study (Time 2), and iv) four months into the study. More frequent sampling was carried out near the beginning of the trial to capture possible onset of tissue inflammation related to diet. The later sampling events were carried out to assess acclimation to the experimental diets. Samples were preserved in 10% buffered formalin, processed routinely, sectioned at 4 µm, stained with hematoxylin and eosin (H&E), and scanned digitally at 40× magnification (Aperio ScanScope). All images were examined blindly by a single aquatic veterinary pathologist (St. George's University, Grenada) and observed tissue alterations were semi-quantitatively scored based on cellular and extracellular changes and inflammatory infiltrates (Tables 16 and 17).

TABLE 16

Histomorphologic scoring key for intestines and pyloric ceca.

| Parameter | Score* | | | | |
|---|---|---|---|---|---|
| | 1 | 2 | 3 | 4 | 5 |
| Supranuclear vacuoles | Abundant and occupy entire area of enterocytes | Abundant and occupy 75% of the enterocyte | Abundant and occupy 50% of the enterocyte | Scattered and occupy less than 10% of enterocyte | No vacuoles observed |

TABLE 16-continued

Histomorphologic scoring key for intestines and pyloric ceca.

| Parameter | Score* | | | | |
|---|---|---|---|---|---|
| | 1 | 2 | 3 | 4 | 5 |
| Goblet cells; Infiltration of eosinophilic granulocytes; Mononuclear cell infiltration | Few observed, scattered | Increased number but widely spread | Moderately densely grouped | Highly abundant and tightly packed | Highly abundant, expanding and replacing normal tissue |

*Semi-quantitative scoring was scored as "1" minimal to "5" server change.

TABLE 17

Histomorphologic scoring key for liver.

| Parameter | Score* | | | | |
|---|---|---|---|---|---|
| | 1 | 2 | 3 | 4 | 5 |
| Hepatocellular lipid and glycogen deposition | Abundant and occupy entire area and expand hepatocytes | Abundant and occupy 75% of the hepatocyte | Abundant and occupy 50% of the hepatocyte | Scattered and occupy less than 10% of the hepatocyte | No vacuoles observed |
| Mononuclear cell infiltration | Few observed, scattered | Increased number but widely spread | Moderately densely grouped | Highly abundant and tightly packed | Highly abundant, expanding and replacing normal tissue |

Water quality sampling and analysis: Water samples were collected from PRAS side drains, bottom drains, and tank inlets at various sampling intervals and tested onsite according to methods described in APHA (2012) and HACH Company (2003; 2015) (Table 18). Dissolved oxygen and water temperature were recorded daily from continuous monitoring systems (Pentair Aquatic Ecosystems, Apopka, Florida, USA; Table 18). In addition, solids removed via the bottom center drains of fish tanks were periodically collected over a 24-h period to assess solids settleability using three portable radial flow settlers. This solids collection procedure was carried out four times during the study: i) prior to feeding experimental diets, ii) two weeks after start-feeding, iii) four months into the trial, and iv) at the end of the study (~6 months). Daily feed amounts were reduced to all PRAS by 30-50% several days prior to these sampling events to reduce the amount of wasted feed mixed with solids samples. Three available radial flow settlers (RFS) were disconnected and moved among PRAS until settleable solids from each replicate system had been collected.

TABLE 18

Water quality parameters evaluated, methodologies for testing and associated equipment, and frequency of data recording/analysis.

| Parameter | Methods and Equipment for Analysis | Approximate Frequency of Recording/Testing |
|---|---|---|
| Dissolved Oxygen & Water Temperature | RDO PRO-X Dissolved Oxygen Probe (In Situ); Point Four™ RIU3 Remote Interface Unit and LC3 Central Water System Monitor/Controller | Daily |
| Carbon Dioxide | In-Situ $CO_2$ Partial Pressure; OxyGuard Portable $CO_2$ Analyzer | Once Weekly |
| Total Ammonia Nitrogen | Hach Method 8038 USEPA Nessler; Spectrophotometers DR2700 and DR6000 | Once Weekly |
| Total Suspended Solids | Standard Methods (2011) 2540D - Dried at 103-105° C. Heratherm Oven #OGS60, Mettler Toledo #AB54S and #PM30K | Once Weekly |
| Particle Size Distribution | Standard Methods (2011) 2560C Light-Blockage Method; Chemtrac PC5000 | Side Drain - 14 events Bottom Drain - 4 events |
| Total Alkalinity | Hach Method 8203 - Sulfuric Acid Digital Titration pH endpoint Accumet #AB150 | Once as background |

TABLE 18-continued

Water quality parameters evaluated, methodologies for testing and associated equipment, and frequency of data recording/analysis.

| Parameter | Methods and Equipment for Analysis | Approximate Frequency of Recording/Testing |
|---|---|---|
| Carbonaceous Biochemical Oxygen Demand | Standard Methods (2011) 5210B - 5-day test (No prefiltration) YSI MultiLab 4010, YSI ProOBOD Sensor; Precision 815 BOD Incubator | Once as background |
| Heterotrophic Bacterial Count | Idexx HPC for Quanti-Tray 2000; Binder Incubator BD56, Idexx Quanti-Tray Sealer, Idexx UV Viewing Cabinet | Twice as background |
| pH | HQ40D Portable Meter; PHC101 probe | Once as background |

Feed disintegration testing: To estimate the direct contribution of the experimental diets to solids concentrations in the PRAS such as dust, fines, or physical breakdown, three replicate benchtop trials were carried out by adding feed samples to specialized mixing jars. Wagner floc jars equipped with a Phipps and Bird stirrer (Richmond, Virginia, USA) were used for feed breakdown testing. Jars were filled with 2 L of tap water, and 50 g of feed per respective diet was weighed into replicate jars. After the feed settled, stirrers were adjusted to 35 rpm to simulate minor turbulence within a fish culture tank. At specified time intervals (5 min and 1 h), water samples were collected from the jars by opening a fixed sampling tap elevated within the water column. Water samples collected from each jar were tested for TSS to estimate the physical contribution of feed pellets to solids in the fish culture system.

Salmon product quality: At the beginning of the study prior to feeding experimental diets, three fish from each PRAS were humanely euthanized for analysis of whole-body proximate composition (percent moisture, crude protein, crude fat, and ash (AOAC, 1995)). Fish were taken off feed three days prior to sampling to ensure that gut contents were fully cleared. At the end of the study, three immature fish from each PRAS were selected for whole-body proximate composition to assess potential differences after feeding the experimental diets for six months. Immature salmon that lacked morphometric characteristics commonly observed as a function of maturation (kyped jaw, dark skin coloration, ovipositor) were selected as representative fish commonly accepted in the marketplace (Aksnes et al., 1986; Michie, 2001). In addition, three immature salmon from each PRAS were filleted and weight measurements were taken to determine head-on-gutted yield, trimmed fillet yield, and gonadosomatic index (gonad weight/whole body weight). Trimmed fillets and viscera were collected in labeled bags for subsequent compositional analyses.

Statistical analysis: Project data were analyzed using Analysis of Variance with post-hoc Tukey's Honest Significant Difference test. Each data set was analyzed for normality using a Shapiro-Wilk test. Non-gaussian distributed data sets were analyzed using the non-parametric Kruskal-Wallis test. A probability level of 0.05 was used to determine significance. All statistical analyses were carried out using SYSTAT 13 software (2009). Replicate fish data per PRAS (n=3) were pooled per treatment (n=9) for proximate composition and fillet yield metrics prior to analysis with ANOVA.

Results

Water Quality: Significant differences in culture tank water quality were detected between diet treatments for the following variables: carbon dioxide ($CO_2$), total ammonia nitrogen (TAN), heterotrophic bacteria count, and total suspended solids (TSS) (Table 19). $CO_2$ and TAN levels measured in PRAS associated with B-FM were significantly greater than levels measured for LAP and B-LAP. Heterotrophic bacteria counts were only assessed twice near the end of the study, but each sample event resulted in significantly greater bacteria counts in PRAS related to LAP compared to all other experimental diets. Significant differences in TSS were detected.

TABLE 19

Water quality concentrations (mean ± standard error (SE)) measured in water samples collected from tank side drains for each diet treatment (n = 3).

| | | No. Sample Events | LAP | FM | B-LAP | B-FM |
|---|---|---|---|---|---|---|
| Carbon Dioxide (mg/L) | * | 25 | 10.5 ± 0.07 | 11.3 ± 0.35 | 10.8 ± 0.06 | 11.7 ± 0.02 |
| Carbonaceous Biochemical Oxygen Demand (mg/L) | | 1 | 1.32 ± 0.40 | 1.76 ± 0.08 | 0.96 ± 0.10 | 1.02 ± 0.06 |
| Dissolved Oxygen (mg/L) | | 187 | 10.4 ± 0.02 | 10.3 ± 0.06 | 10.5 ± 0.04 | 10.3 ± 0.05 |
| Heterotrophic Bacteria (counts/100 mL) | * | 2 | 150,053 | 50,827 | 57,133 | 18,553 |
| pH (s.u.) | | 1 | 7.54 ± 0.007 | 7.52 ± 0.015 | 7.53 ± 0.003 | 7.54 ± 0.009 |
| Temperature (° C.) | | 187 | 13.3 ± 0.02 | 13.3 ± 0.05 | 13.2 ± 0.07 | 13.4 ± 0.07 |

TABLE 19-continued

Water quality concentrations (mean ± standard error (SE)) measured in water samples collected from tank side drains for each diet treatment (n = 3).

| | No. Sample Events | | LAP | FM | B-LAP | B-FM |
|---|---|---|---|---|---|---|
| Total Alkalinity (mg/L) | | 1 | 278 ± 1.2 | 274 ± 1.7 | 277 ± 1.3 | 278 ± 1.3 |
| Total Ammonia Nitrogen (mg/L) | * | 27 | 0.23 ± 0.004 | 0.31 ± 0.003 | 0.23 ± 0.003 | 0.27 ± 0.012 |
| Total Suspended Solids (mg/L) | * | 28 | 1.10 ± 0.03 | 1.36 ± 0.06 | 0.69 ± 0.02 | 0.70 ± 0.02 |

* Indicates significant different between treatments

Figure 10:
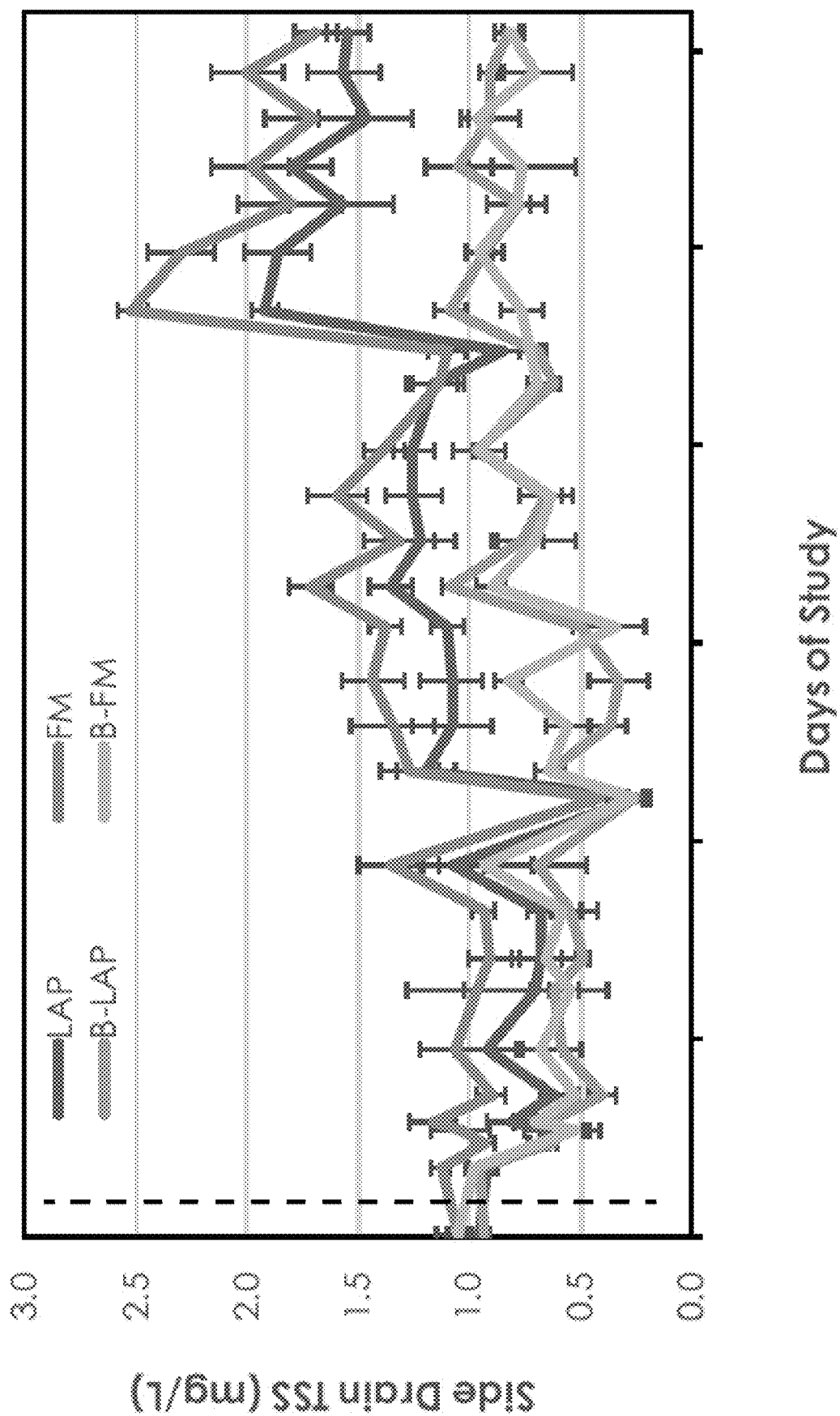
FIG. 10 shows total suspended solids concentrations (mean±SE) measured in water samples collected from tank side drains throughout the study. The dotted line indicates start-feeding of experimental diets.
Figure 11:
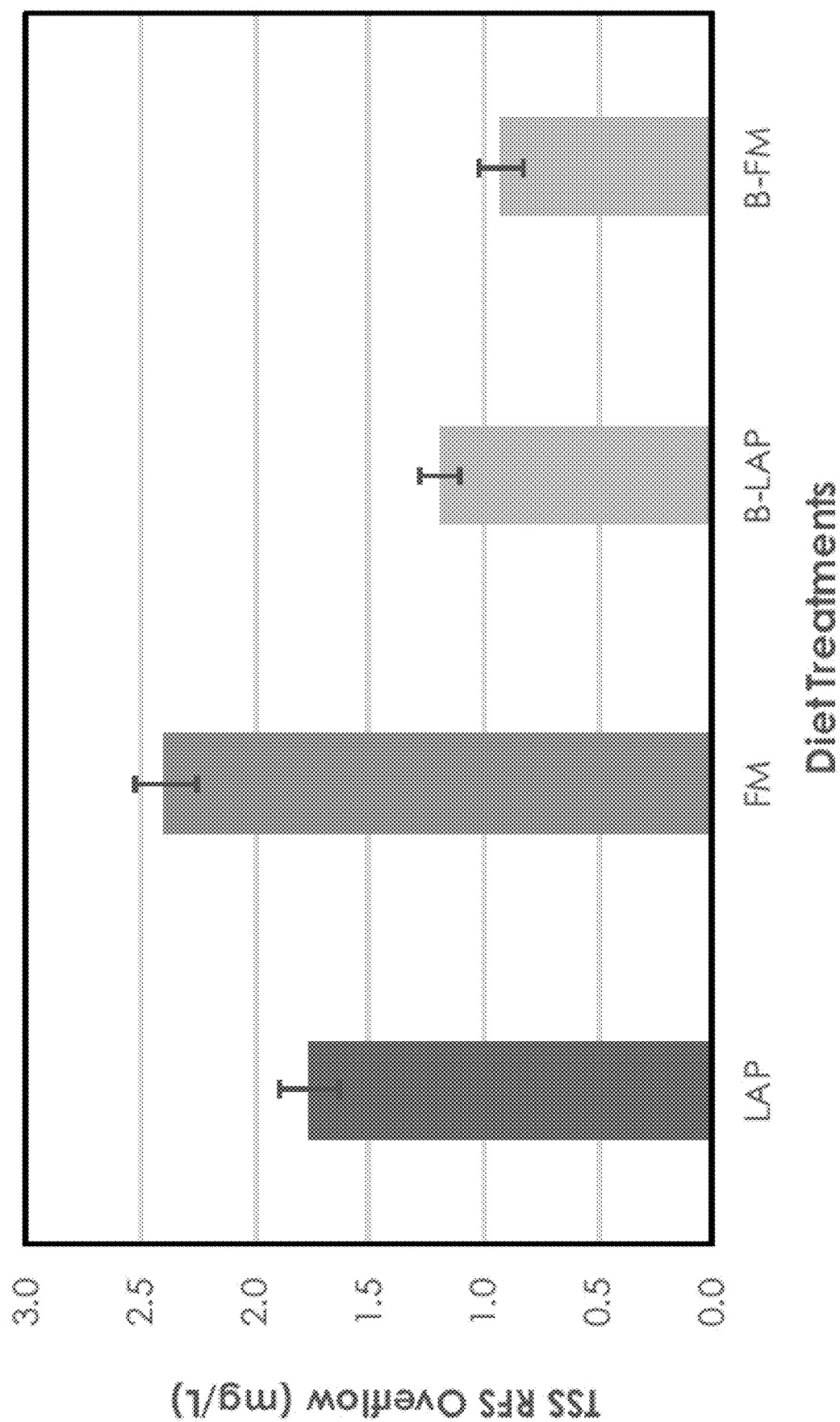
FIG. 11 shows total suspended solids concentrations (mean±SE) measured in water samples collected from the "clean" overflow of the radial flow settlers during corresponding solids collection events. These data represent the average of results collected during the final two solids collection events.
Figure 12:
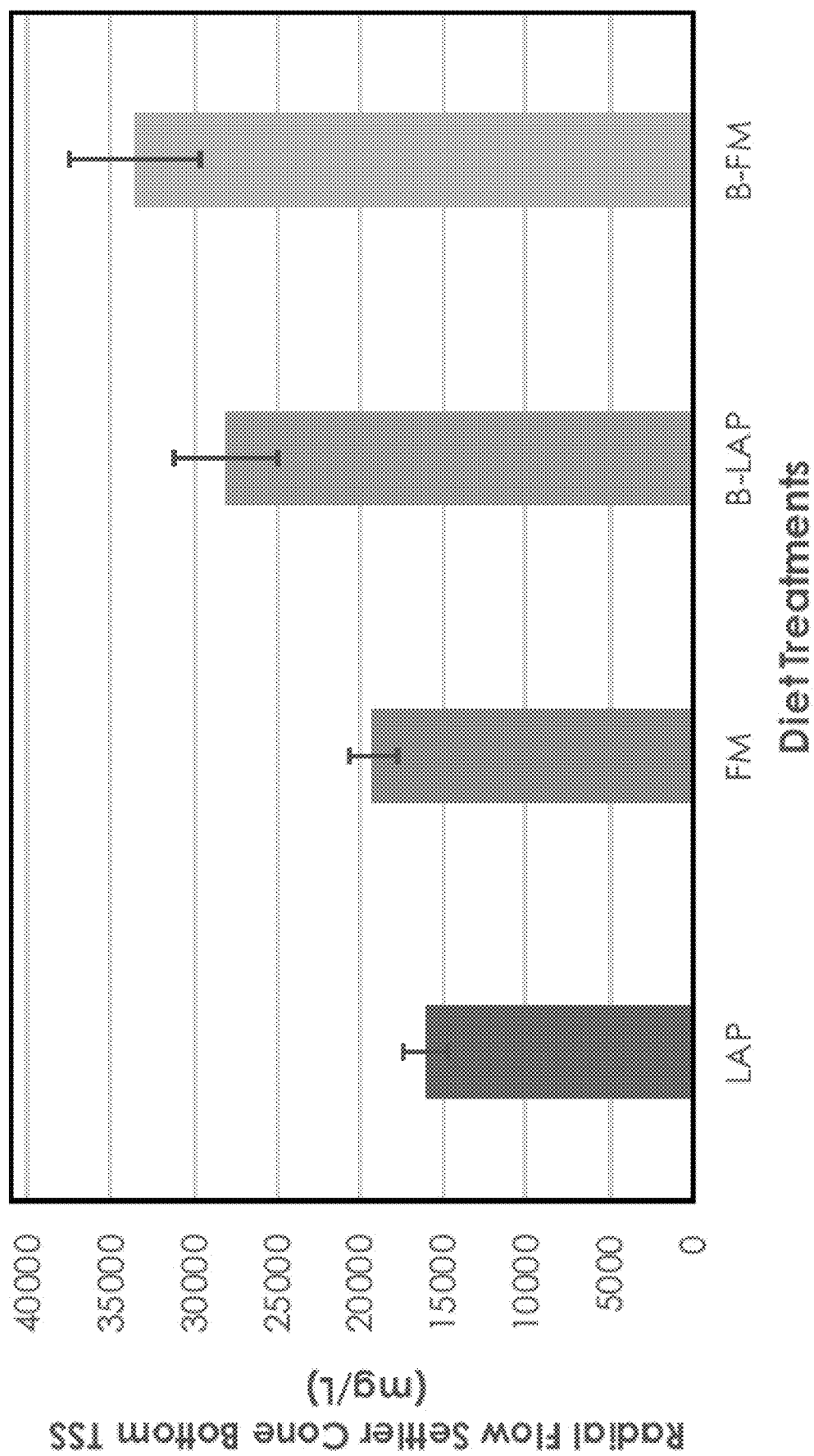
FIG. 12 shows total suspended solids concentrations (mean±SE) measured in water samples collected from the cone bottoms of radial flow settlers over 24 hours. These data represent the mean of three solids collection events carried out over the course of the study.

Total Suspended Solids: A detailed TSS assessment was carried out at key sampling locations in each PRAS. Mean TSS concentrations for diets FM and LAP were significantly higher than B-FM and B-LAP at all sample sites including the tank side drain, bottom drain, and inlet, as well as the overflow of radial flow settlers (RFS) (Table 20; FIGS. 10-12). The FM diet resulted in the greatest TSS concentrations at each of these sampling locations. Fine solids overflowing the RFS weirs were observed for diets FM and LAP. This observation was reflected in the TSS values at the RFS Overflow (Table 20; FIG. 11). Conversely, diet B-FM had significantly greater TSS in the flow flushed from the bottom of the radial flow settler compared to LAP and FM, and the TSS values measured for B-LAP bordered statistical difference for this metric (Table 20; FIG. 12). These results suggest greater TSS settleability for diets B-FM and B-LAP where approximately 40% more TSS was captured in the RFS settling cone for these diets compared to the two diets that lacked locust bean gum.

TABLE 20

Total suspended solids concentrations (mean ± SE) measured in water samples collected from various PRAS locations for each diet treatment (n = 3).

| No. Sample Events | | | LAP | FM | B-LAP | B-FM |
|---|---|---|---|---|---|---|
| Side Drain | * | 28 | 1.11 ± 0.02 | 1.37 ± 0.06 | 0.69 ± 0.02 | 0.70 ± 0.02 |
| Bottom Drain | * | 28 | 1.92 ± 0.06 | 2.49 ± 0.05 | 1.25 ± 0.13 | 0.98 ± 0.08 |
| Tank Inlet (Reuse) | * | 5 | 1.55 ± 0.05 | 1.85 ± 0.07 | 0.99 ± 0.14 | 0.91 ± 0.08 |
| RFS Overflow | * | 2 | 1.76 ± 0.12 | 2.40 ± 0.13 | 1.20 ± 0.09 | 0.92 ± 0.10 |
| RFS Cone Bottom † | * | 3 | 16,069 | 19,232 | 28,085 | 33,584 |

Figure 13:
FIG. 13 shows FM diet (no binding agent) after 1-hour submergence and mixing showing visual evidence of pellet instability, disintegration.

Feed disintegration testing: Three repeat bench-top trials were carried out to evaluate the rate of feed breakdown and associated stability of diets using a specialized mixing apparatus. Development of TSS in the water columns of mixing jars revealed two separate time-dependent responses. Short-term (5-min) submergence and mixing resulted in significantly greater TSS in the water column for the FM diet compared to LAP with a trend towards significance between FM and B-LAP (Table 21). A trend existed for a rapid increase in TSS for FM-based diets, possibly due to more associated dry fines. No significant differences in TSS were evident after one hour of mixing; however, TSS was generally greater in the mixing columns for diets that lacked the locust bean gum (FIG. 13).

TABLE 21

TSS (mean ± SE) resulting from submergence, mixing, and associated breakdown of diets in a static container. Data is an average of three repeat trials for each experimental diet.

TSS (mg/L)

| Time Interval | P < 0.05 | LAP | FM | B-LAP | B-FM |
|---|---|---|---|---|---|
| 5-min | * | 3.0 ± 0.4 | 19.7 ± 3.1 | 8.0 ± 3.9 | 13.5 ± 2.5 |
| 1-hour | | 31.0 ± 15.9 | 38.8 ± 8.8 | 20.8 ± 3.2 | 21.2 ± 1.6 |

* Indicates significant difference between treatments

Figure 14:
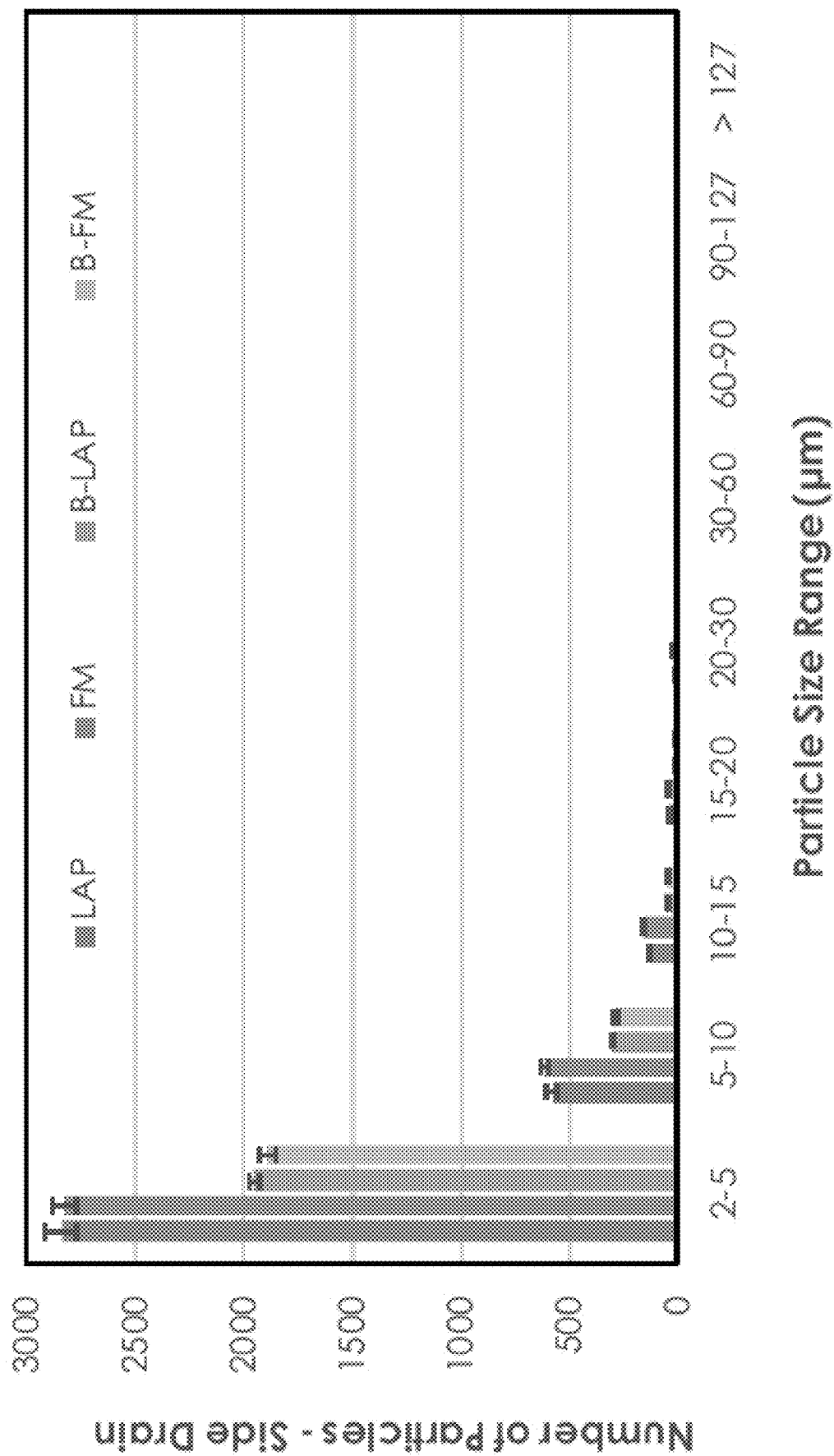
FIG. 14 shows mean particle size distribution (mean±SE) from water samples collected from PRAS side drains for each diet treatment over the duration of the study (n=3).

Particles size distribution: A highly significant difference (P=0.000) in mean particle counts in the fish culture water was detected within every analyzed size category comparison between diets with (FM, LAP) and without (B-FM, B-LAP) the locust bean gum (FIG. 14; Table 22). On average, the total number of particle-counts for diets B-FM and B-LAP was 35-40% lower than FM and LAP. The majority of particles counted for each diet treatment were <20 μm in size, with small particles in the 2-5 μm range dominating the size spectrum (FIG. 14).

TABLE 22

Statistical P-values resulting from ANOVA and post-hoc analysis for each diet treatment comparison and within each tested particle size category.
Tukey's Pairwise Comparison P-values

| Diet Comparison | | 2-5 µm | 5-10 µm | 10-15 µm | 15-20 µm | 20-30 µm | 30-60 µm | 60-90 µm | Total Particles |
|---|---|---|---|---|---|---|---|---|---|
| LAP | FM | 0.995 | 0.447 | 0.005 * | 0.002 * | 0.021 * | 0.371 | 0.463 | 0.927 |
| LAP | B-LAP | 0.000 * | 0.000 * | 0.000 * | 0.000 * | 0.000 * | 0.000 * | 0.000 * | 0.000 * |
| LAP | B-FM | 0.000 * | 0.000 * | 0.000 * | 0.000 * | 0.000 * | 0.000 * | 0.000 * | 0.000 * |
| FM | B-LAP | 0.000 * | 0.000 * | 0.000 * | 0.000 * | 0.000 * | 0.000 * | 0.000 * | 0.000 * |
| FM | B-FM | 0.000 * | 0.000 * | 0.000 * | 0.000 * | 0.000 * | 0.000 * | 0.000 * | 0.000 * |
| B-LAP | B-FM | 0.844 | 0.876 | 0.902 | 0.963 | 1.000 | 0.997 | 0.994 | 0.857 |

* Indicates significant difference between treatments

Fish performance: To begin the study, mean weights of Atlantic salmon from each diet treatment were statistically similar, as was expected due to effective randomization of fish during stocking. Overall, inclusion of locust bean gum in the experimental diets did not affect salmon growth.

Fish health: Cumulative survival was not affected by diet treatment. In fact, survival was excellent for all treatments ranging from 97.9-98.5%. In addition, no important differences in tissue histopathology scores were identified for the distal intestine, pyloric ceca, or liver (Tables 23-25).

TABLE 23

Mean (±SE) scoring for observed lesions * in distal intestine at each sampling event.

| Diet | Time | Supranuclear vacuole density | Goblet cell density | Eosinophilic granular cell infiltration | Mononuclear cell infiltration |
|---|---|---|---|---|---|
| LAP | 0 | 1.53 ± 0.18 | 2.27 ± 0.07 | 3.33 ± 0.07 | 1.27 ± 0.07 |
|  | 1 | 1.40 ± 0.12 | 2.53 ± 0.13 | 3.47 ± 0.13 | 1.27 ± 0.07 |
|  | 2 | 1.40 ± 0.31 | 2.53 ± 0.18 | 3.47 ± 0.13 | 1.20 ± 0.12 |
| FM | 0 | 1.47 ± 0.13 | 2.27 ± 0.18 | 3.47 ± 0.07 | 1.13 ± 0.13 |
|  | 1 | 1.47 ± 0.37 | 2.67 ± 0.07 | 3.47 ± 0.07 | 1.40 ± 0.12 |
|  | 2 | 1.67 ± 0.33 | 2.53 ± 0.07 | 3.53 ± 0.07 | 1.33 ± 0.07 |
| B-LAP | 0 | 1.07 ± 0.07 | 2.33 ± 0.07 | 3.13 ± 0.07 | 1.47 ± 0.07 |
|  | 1 | 1.47 ± 0.27 | 2.60 ± 0.12 | 3.13 ± 0.13 | 1.40 ± 0.31 |
|  | 2 | 1.90 ± 0.5 | 2.50 ± 0.10 | 3.70 ± 0.10 | 1.20 ± 0.00 |
| B-FM | 0 | 1.27 ± 0.18 | 2.40 ± 0.12 | 3.33 ± 0.13 | 1.33 ± 0.13 |
|  | 1 | 1.60 ± 0.50 | 2.67 ± 0.13 | 3.47 ± 0.13 | 1.27 ± 0.07 |
|  | 2 | 1.93 ± 0.27 | 2.53 ± 0.13 | 3.27 ± 0.07 | 1.27 ± 0.07 |

* No significant ($P < 0.05$) differences in lesion severity among diet treatments within each sampling event.

TABLE 24

Mean (±SE) scoring for observed lesions * in pyloric ceca at each sampling event.

| Diet | Time | Supranuclear vacuole density | Goblet cell density | Eosinophilic granular cell infiltration | Mononuclear cell infiltration |
|---|---|---|---|---|---|
| LAP | 0 | 2.05 ± 0.15 | 2.13 ± 0.07 | 2.87 ± 0.47 | 1.00 ± 0.00 |
|  | 1 | 2.13 ± 0.18 | 2.73 ± 0.13 | 3.53 ± 0.13 | 1.00 ± 0.00 |
|  | 2 | 1.73 ± 0.29 | 2.73 ± 0.18 | 3.33 ± 0.13 | 1.00 ± 0.00 |
| FM | 0 | 1.87 ± 0.18 | 2.20 ± 0.00 | 2.73 ± 0.33 | 1.00 ± 0.00 |
|  | 1 | 1.80 ± 0.12 | 2.53 ± 0.18 | 3.53 ± 0.13 | 1.00 ± 0.00 |
|  | 2 | 1.67 ± 0.37 | 2.67 ± 0.07 | 3.13 ± 0.07 | 1.00 ± 0.00 |
| B-LAP | 0 | 1.80 ± 0.00 | 2.27 ± 0.07 | 3.40 ± 0.31 | 1.00 ± 0.00 |
|  | 1 | 2.00 ± 0.31 | 2.53 ± 0.13 | 3.13 ± 0.24 | 1.07 ± 0.07 |
|  | 2 | 1.80 ± 0.00 | 2.80 ± 0.00 | 3.27 ± 0.18 | 1.00 ± 0.00 |
| B-FM | 0 | 1.77 ± 0.15 | 2.22 ± 0.12 | 2.85 ± 0.45 | 1.00 ± 0.00 |
|  | 1 | 1.93 ± 0.24 | 2.80 ± 0.12 | 3.47 ± 0.07 | 1.00 ± 0.00 |
|  | 2 | 1.87 ± 0.18 | 2.73 ± 0.13 | 3.67 ± 0.13 | 1.00 ± 0.00 |

* No significant ($P < 0.05$) differences in lesion severity among diet treatments within each sampling event.

TABLE 25

Mean (±SE) scoring for observed lesions * in livers at each sampling event

| Diet | Time | Hepatocellula lipid/ glycogen deposition * | Mononuclear cell infiltrates | Other specific hepatic lesions ** |
|---|---|---|---|---|
| LAP | 0 | 3.45 ± 0.16 | 1.00 ± 0.00 | Not observed |
|  | 1 | 3.80 ± 0.13 | 1.00 ± 0.00 | Not observed |
|  | 2 | 3.20 ± 0.10 | 1.00 ± 0.00 | Not observed |
| FM | 0 | 3.07 ± 0.13 | 1.00 ± 0.00 | Not observed |
|  | 1 | 3.93 ± 0.29 | 1.00 ± 0.00 | Not observed |
|  | 2 | 3.50 ± 0.10 | 1.00 ± 0.00 | Not observed |
| B-LAP | 0 | 3.20 ± 0.12 | 1.00 ± 0.00 | Not observed |
|  | 1 | 3.73 ± 0.27 | 1.00 ± 0.00 | Not observed |
|  | 2 | 3.30 ± 0.10 | 1.00 ± 0.00 | Not observed |
| B-FM | 0 | 3.67 ± 0.37 | 1.00 ± 0.00 | Not observed |
|  | 1 | 3.60 ± 0.12 | 1.00 ± 0.00 | Not observed |
|  | 2 | 3.50 ± 0.10 | 1.00 ± 0.00 | Not observed |

* No significant ($P < 0.05$) differences in lesion severity among diet treatments within each sampling event.
** Other specific hepatic lesions examined: eosinophilic granular cell infiltrates, focal hepatocellular vacuolation, hepatocellular megalocytosis not due to vacuolation, hepatic nuclear pleomorphism, hepatocellular karyomegaly, oval cell proliferation, bile duct/ductile hyperplasia, vacuolation of biliary epithelium, hepatocellular regeneration, necrosis, and fibrosis.

Product Quality: Fish sampled for baseline whole-body proximate composition prior to feeding the experimental diets were 49±1 cm long and weighed 1.591±0.057 kg. Baseline proximate compositional analysis yielded the following results: 81.8±0.2% moisture, 19.1±0.2% protein, 10.4±0.3% fat, and 2.20±0.03% ash. No significant differences were detected in the proximate composition of fish that were randomized among intended diet treatments. Whole-body proximate compositional analysis was repeated at the conclusion of the study, as well as analyses to assess the composition of fillets and viscera to determine if there were differences in lipid compartmentalization between diet treatments. Immature salmon of similar size (3.776±0.080 kg) were selected during these sampling events to reduce variation created by maturation and growth. Fillet processing and yield data was collected at the time of sampling for proximate composition. Head-on-gutted and trimmed (skin-on) fillet processing yield was not affected by diet treatment for fish of similar size and maturity status (Table 26).

TABLE 26

Processing yield and proximate compositional analysis (mean ± SE) from fillets and viscera for fish sampled at the conclusion of the study after receiving the experimental diets for six months.

| Diet Treatment | LAP | FM | B-LAP | B-FM |
|---|---|---|---|---|
| Gonadosomatic In-dex (%) | 1.12 ± 0.45 | 1.19 ± 0.48 | 0.85 ± 0.16 | 0.79 ± 0.16 |
| Head-On-Gutted Yield (%) | 90.0 ± 0.4 | 90.4 ± 0.5 | 90.0 ± 0.4 | 90.7 ± 0.4 |
| Trimmed Fillet Yield (%) | 59.8 ± 0.4 | 60.8 ± 0.5 | 59.9 ± 0.5 | 61.2 ± 0.5 |

Maturation: The majority of salmon utilized in this trial matured by study's end. Percent maturity as reflected by notation of obvious morphometric characteristics (kype jaw, ovipositor, skin coloration) ranged from 78.6-84.3%, and mean maturity of all sampled fish was 80.7±1.5% at study's end. Male salmon were easily recognized by a hooked jaw (kype) and bronze skin coloration, while maturing female salmon were identified based on the presence of an ovipositor (egg laying organ located at the vent) as well as dark skin coloration with red spots and a distended abdomen. Immature fish had silver skin coloration and lacked the other descriptors common to maturing fish.

CONCLUSIONS

This 2×2 factorial study resulted in two profound responses between dietary treatments: i) water quality differences (most importantly TSS concentrations and particle counts) and ii) Atlantic salmon growth performance metrics. Diets that included locust bean gum (B-LAP and B-FM) resulted in significantly lower TSS levels and particle counts in the fish culture water and greater TSS collected from the cone-bottom of radial flow settlers. These findings indicate that the locust bean gum was effective at increasing the stability and settleability of fish fecal matter. Atlantic salmon growth was not affected by inclusion of the locust bean gum.

Water Quality: Fine solids can have a magnified effect in RAS because they can readily accumulate in the fish culture water compared to heavily flushed or open production systems. Accumulating solids are harmful for fish health and can negatively impact the performance of water treatment processes such as biofilters (Zhu and Chen, 2001). Therefore, aquafeeds purposed for fish within RAS must be compatible with fish health and performance, as well as the culture system technology. One aspect of the present study was to evaluate the effect of locust bean gum on fish fecal stability and resulting water quality within water reuse systems. PRAS associated with diets containing the locust bean gum (B-FM and B-LAP) contained substantially lower TSS in the fish production water.

In addition, solids collection data indicated that a greater concentration of TSS was collected in settler devices for B-FM and B-LAP diets. Interestingly, the solids ratios in the RFS overflow and RFS cone-bottom for diets with and without the locust bean gum are nearly opposite, as depicted in FIGS. 11 and 12. Specifically, the extra solids that appear to have been collected by the radial flow settlers for diets B-FM and B-LAP otherwise remain buoyant and in suspension within the RFS and the fish culture water for diets that lacked the binder-like ingredient (FM and LAP). Prior to having knowledge of the experimental treatments, fish culture staff observed that solids collected in RFS for diet B-FM were noticeably stringy and intact.

The differences in TSS noted between dietary treatments extended to particle count data, where diets that lacked the locust bean gum resulted in substantially greater particle counts in the fish culture water. The majority of particles counted for both diet treatments were <20 μm, and therefore would pass through common solids filtration equipment such as drum filters which are generally equipped with microscreens with 60 μm pore size. However, this particle size distribution (PSD) is relatively common for RAS, as similar PSD trends with large percentages of microparticles have been reported in other experiments (Patterson and Watts, 2003; Davidson et al., 2011; Fernandes et al., 2014). It should be noted that drum filters were not included in the water recycle loop of replicate PRAS used during this study. In the experimental PRAS, accumulation of fine particles was limited by continuous dilution (11% of the recycle flow); however, in a RAS with low water exchange and long hydraulic retention time, buildup of fine particles in the culture water is expected.

Feed breakdown was also briefly evaluated to understand whether solids accumulation was resulting from fish fecal waste or physical properties of the diets themselves such as dry fines or disintegration of feed pellets. All diets that remained submerged in water of specialized mixing jars for 1-h began to disintegrate resulting in increased total suspended solids levels in the water column. A trend was evident that indicated greater stability of feed pellets that contained the binder-like additive. Wasted feed pellets will flush from RAS tanks within seconds to minutes after entering the water column (Davidson and Summerfelt, 2004); however, collected feed may be stored for hours within settling devices before being flushed from the system. As evidenced in the feed breakdown tests carried out during the present study, stored wasted feed particles were disintegrating and leaching solids. Disintegrating feed could also release other nutrients such as nitrogen, phosphorous, and dissolved metals. Therefore, long term stability of submerged feed pellets is also advantageous in RAS. An additional piece of information was also gleaned from these pellet stability tests; whereas, FM-based diets tended to result in greater TSS in the mixing jars after just five minutes of submergence. The authors hypothesize that this TSS response could have been related to dry fines or dust particles associated with the FM-based diet formulations. This phenomenon did not extend to TSS measured in the fish culture systems.

Other water quality variables were also found to be significantly different between treatments including TAN and $CO_2$, where TAN and $CO_2$ were generally greater in PRAS associated with FM diets. Increased levels of these constituents in the culture water of FM and B-FM was likely related to increased feeding, growth, and associated metabolism, as it has been well documented that fish produce a certain amount of waste per kg feed consumed (Davidson et al., 2016b; Timmons et al., 2018). Salmon that received fishmeal-based diets grew faster and appeared to consume more feed based on FCR data and observations of wasted feed collecting in the radial flow settlers; therefore, the slightly greater metabolite concentrations measured in the culture water associated with FM-based diets is not surprising. The differences in TAN and $CO_2$ measured between treatments during the present study were relatively small in magnitude and were insignificant to salmonid health and performance (Wedemeyer, 1996; Good et al., 2018). Although $CBOD_5$ was not statistically different there was a trend for increased $CBOD_5$ in the culture water associated with diets that lacked the binder-like ingredient (FM and LAP). Biochemical oxygen demand is the amount of oxygen required for microbial metabolism of organic matter present in the water. Although, there was not a significant difference in $CBOD_5$ measured between diet treatments, the observed trend suggests that diets that lacked the binder-like ingredient would impart a greater oxygen demand in a water reuse system, thereby leading to greater oxygen use and associated expenditures. Increased solids and organic matter present in PRAS associated with LAP may have supported the significantly higher heterotrophic bacteria measured in these systems near the end of the study. While there was not evidence of pathogenic bacteria existing as part of the total heterotrophic bacteria load, increased solids and organic matter can also create a substrate for pathogens (Liltved and Cripps, 1999; Cripps and Bergheim, 2000).

Fish Performance: The base diet that was fed to fish in all PRAS prior to the study was a standard North American formula (EWOS Dynamic Red, Cargill Inc.) that included LAP. This diet formulation served as the basis for development of the experimental diets used in the present study. A skilled artisan will recognize that slight changes to diet formulations are common when switching feed sizes within a specific product line. In the case of the present study, Atlantic salmon were fed an 8 mm EWOS Dynamic Red leading up to the experiment, and then were switched abruptly to the test diets in a 10.5 mm pellet size.

Results of histopathology assessments were largely unremarkable and indicated neither differences in inflammatory response to specific diets nor unusual tissue responses in general when compared to previous research. A previous study examining Atlantic salmon health and performance when fed experimental diets formulated with either fishmeal- or non-fishmeal based-proteins demonstrated intestinal pathology scores that were actually higher on average (i.e., greater inflammation observed), regardless of diet treatment, than those typically observed in the present study. In the absence of any observed, significant intestinal inflammation or liver pathologies among and between the four diet groups in the present study, underlying pathological processes were most likely not influencing the feed conversion and growth performance differences noted.

Early salmon maturation is a common problem observed in RAS (Good and Davidson, 2016). Salmon maturation is a highly flexible process that is influenced by a variety of factors including water temperature, photoperiod, and fish genetics, among others (Good and Davidson, 2016). Of the various Atlantic salmon strains that have been evaluated onsite, the genetic line used during this study has been the most prone to early maturity. The high degree of maturation that was observed during this study may not be representative of the expected maturation percentage in land-based RAS; however, early maturation occurred at an equal rate for all diet treatments and therefore did not confound the responses observed during this trial.

Product Quality: Previous studies indicate that balanced diet formulations that utilize replacement proteins including LAP do not affect important product quality metrics. For example, during a previous study comparing a fishmeal-free diet with LAP versus a fishmeal-based diet fed to post-smolt Atlantic salmon, Davidson et al. (2017) found no effects on processing yield, fillet proximate composition, and primary whole-body proximate composition metrics (moisture, protein, fat). The only significant response identified during the Davidson et al. (2017) trial was greater whole-body ash content in Atlantic salmon fed the fishmeal-free diet with LAP. Likewise, Foroutani et al. (2018) found that diets with a range of replacement ingredients for fishmeal, including LAP, did not affect the total lipid content in Atlantic salmon smolt flesh.

Example 8

The test feeds for this example are based on the reference diet base mix containing 53.3% protein and 19.9% fat. The detailed formulation of the reference diet base mix is given in Table 2 and diet formulations with binding agents in this Example are outlined in Table 27 and feed composition in Table 28. The extruded feeds had a pellet diameter of 4 mm.

TABLE 27

Diet formulations with binding agents.

| | % of diet (weight %) | | | | |
|---|---|---|---|---|---|
| | 0.5% Gg | 0.5% Css | 1.0% Css | 0.3% Css & 0.2% Xnth | 0.2% Css & 0.3% Xnth |
| Guar Gum | 0.50 | | | | |
| Cassia gum | | 0.50 | 1.00 | 0.30 | 0.20 |
| Xanthan gum | | | | 0.20 | 0.30 |
| Fish meal | 71.49 | 71.49 | 71.07 | 71.49 | 71.49 |
| Wheat grain | 14.51 | 14.51 | 14.43 | 14.51 | 14.51 |
| Additives | 0.48 | 0.48 | 0.48 | 0.48 | 0.48 |
| Rapeseed oil | 6.51 | 6.51 | 6.51 | 6.51 | 6.51 |
| Fish oil | 6.51 | 6.51 | 6.51 | 6.51 | 6.51 |
| Total | 100.00 | 100.00 | 100.00 | 100.00 | 100.00 |

TABLE 28

Trial feed analyzed composition.

| | FMRef | 0.5% Gg | 0.5% Css | 1.0% Css | 0.3% Css & 0.2% Xnth | 0.2% Css & 0.3% Xnth |
|---|---|---|---|---|---|---|
| Protein (%; Dumas) | 53.3 | 53.4 | 52.7 | 53.5 | 52.9 | 54.5 |
| Fat (%; LfNMR) | 19.9 | 19.8 | 20.1 | 19.9 | 19.8 | 19.7 |
| Moisture (%) | 6.4 | 7.5 | 7.6 | 6.6 | 8.0 | 6.0 |
| Ash (%) | 11.6 | 11.5 | 11.6 | 11.6 | 11.2 | 11.7 |
| Yttrium (mg/kg; XRF) | 106 | 114 | 116 | 126 | 122 | 122 |

Atlantic salmon were stocked in four replicate freshwater tanks per diet with 60 fish per tank and estimated to be about 190 g at time of feces sampling. Water temperature averaged 13.9° C. during the feces sampling week. Fresh feces were collected from each tank over three separate days after at least one week of acclimation feeding on trial diets. Feces binding was measured as a percentage of particles greater than 50 μm after 5 minutes of stirring as determined using laser diffraction on a Mastersizer. This measurement of feces binding represents the feces particles that can be removed by mechanical filtration. The particle size and digestibility analysis methods are the same as those outlined in Example 1.

Figure 15:
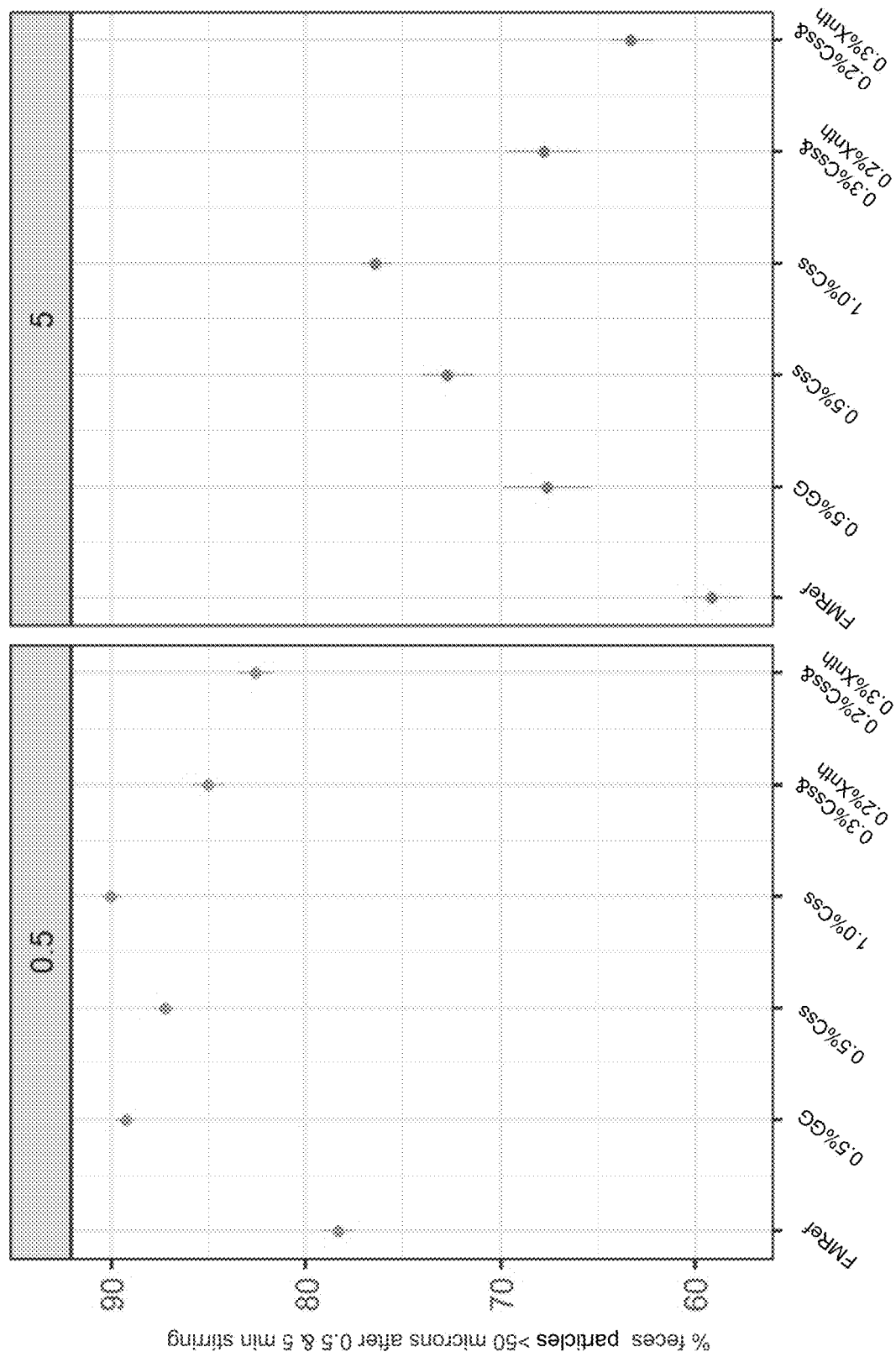
FIG. 15 shows percent of feces particles greater than 50 μm after 0.5 (left) and 5 (right) minutes of stirring in Mastersizer based on the fish feed formulations outlined in Example 8.

FIG. 15 shows the percent of feces particles greater than 50 μm after 0.5 minutes (left) and 5 minutes (right) of stirring at 2500 rpm. All the trial diets showed significant increases in feces particle size after 5 minutes as compared to the base diet. Note that the percent of feces particles greater than 50 μm at 5 min for one of four tank replicates on FMRef diet was missing and extrapolated from the other 9 points in the time series using a logarithmic equation.

Figure 16:
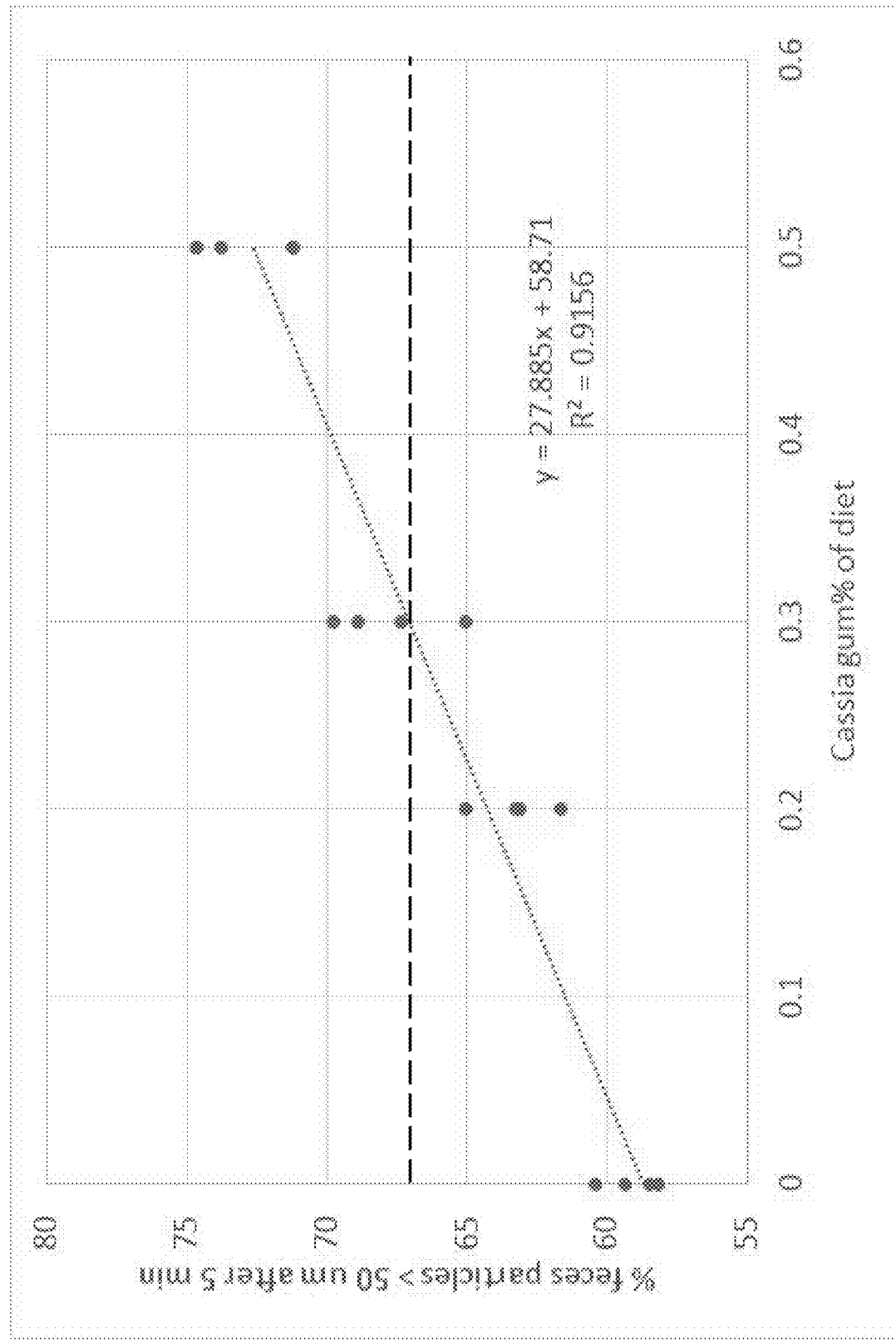
FIG. 16 shows the percent of feces particles greater than 50 μm after 5 minutes of stirring in Mastersizer as a function of the cassia gum concentration as outlined in Example 8.

FIG. 16 shows the relationship between feces binding and cassia gum dose in the trial feed. The data show that there is a linear trend for feces binding with increased cassia gum inclusion up to 0.5% of the diet (assuming no effect from the xanthan gum in the combined treatments). Above 0.5% inclusion there is a flattening to 1.0% of diet (not shown). The data in FIG. 16 is from 4 replicate tanks taken as the average of 3 samples per tank. 67.0% of feces particles were greater than 50 microns after 5 minutes for diets with 0.5% guar gum (overall tank average; dashed line in FIG. 16) which is equivalent to the feces binding in diets with 0.3% cassia gum.

Protein digestibility was highest for FMRef diet but all feeds were within 0.7 percentage points as feed median. Fat digestibility had higher 1.6 percentage point range between feeds as feed median without any negative effect of 0.5 or 1.0% cassia gum diets (no xanthan gum added to these feeds with cassia gum) but negative fat digestibility trend observed for the combined cassia gum/xanthan gum diets on fat digestibility versus FMRef diet. Dry matter digestibility was nominally highest for FMRef diet but all feeds were within 1.0 percentage point range as feed median.

Example 9

The test feeds for this example are based on the reference diet base mix containing 53.3% protein and 19.9% fat. The detailed formulation of the reference diet base mix is given in Table 2 and diet formulations with binding agents in this Example are outlined in Table 29 and feed composition in Table 30. The extruded feeds had a pellet diameter of 4 mm.

TABLE 29

Diet formulations with binding agents.

| | % of diet (weight %) | | | | | |
|---|---|---|---|---|---|---|
| | 0.5% Gg | 0.5% Psyl | 0.75% Psyl | 1.0% Psyl | 0.5% Kry | 1.0% Kry |
| Guar Gum | 0.50 | | | | | |
| Psyllium husk powder | | 0.50 | 0.75 | 1.00 | | |
| Karaya gum | | | | | 0.50 | 1.00 |
| Fish meal | 71.49 | 71.49 | 71.28 | 71.07 | 71.49 | 71.07 |
| Wheat grain | 14.51 | 14.51 | 14.47 | 14.43 | 14.51 | 14.43 |
| Additives | 0.48 | 0.48 | 0.48 | 0.48 | 0.48 | 0.48 |

TABLE 29-continued

Diet formulations with binding agents.

| | % of diet (weight %) | | | | | |
|---|---|---|---|---|---|---|
| | 0.5% Gg | 0.5% Psyl | 0.75% Psyl | 1.0% Psyl | 0.5% Kry | 1.0% Kry |
| Rapeseed oil | 6.51 | 6.51 | 6.51 | 6.51 | 6.51 | 6.51 |
| Fish oil | 6.51 | 6.51 | 6.51 | 6.51 | 6.51 | 6.51 |
| Total | 100.00 | 100.00 | 100.00 | 100.00 | 100.00 | 100.00 |

TABLE 30

Trial feed analyzed composition.

| | 0.5% Gg | 0.5% Psyl | 0.75% Psyl | 1.0% Psyl | 0.5% Kry | 1.0% Kry |
|---|---|---|---|---|---|---|
| Protein (%; Dumas) | 53.4 | 52.8 | 52.9 | 52.1 | 54.6 | 51.6 |
| Fat (%; LfNMR) | 19.8 | 19.9 | 19.6 | 20.1 | 19.7 | 19.5 |
| Moisture (%) | 7.5 | 6.5 | 7.0 | 7.7 | 5.6 | 8.3 |
| Ash (%) | 11.5 | 11.7 | 11.6 | 11.8 | 11.9 | 11.3 |
| Yttrium (mg/kg; XRF) | 114 | 125 | 122 | 117 | 122 | 117 |

Atlantic salmon were stocked in four replicate freshwater tanks per diet with 60 fish per tank and estimated to be about 280 g at time of feces sampling. Water temperature averaged 13.9° C. during the feces sampling week. Fresh feces were collected from each tank over three separate days after at least one week of acclimation feeding on trial diets. Feces binding was measured as a percentage of particles greater than 50 μm after 5 minutes of stirring as determined using laser diffraction on a Mastersizer. This measurement of feces binding represents the feces particles that can be removed by mechanical filtration. The particle size and digestibility analysis methods are the same as those outlined in Example 1.

Figure 17:
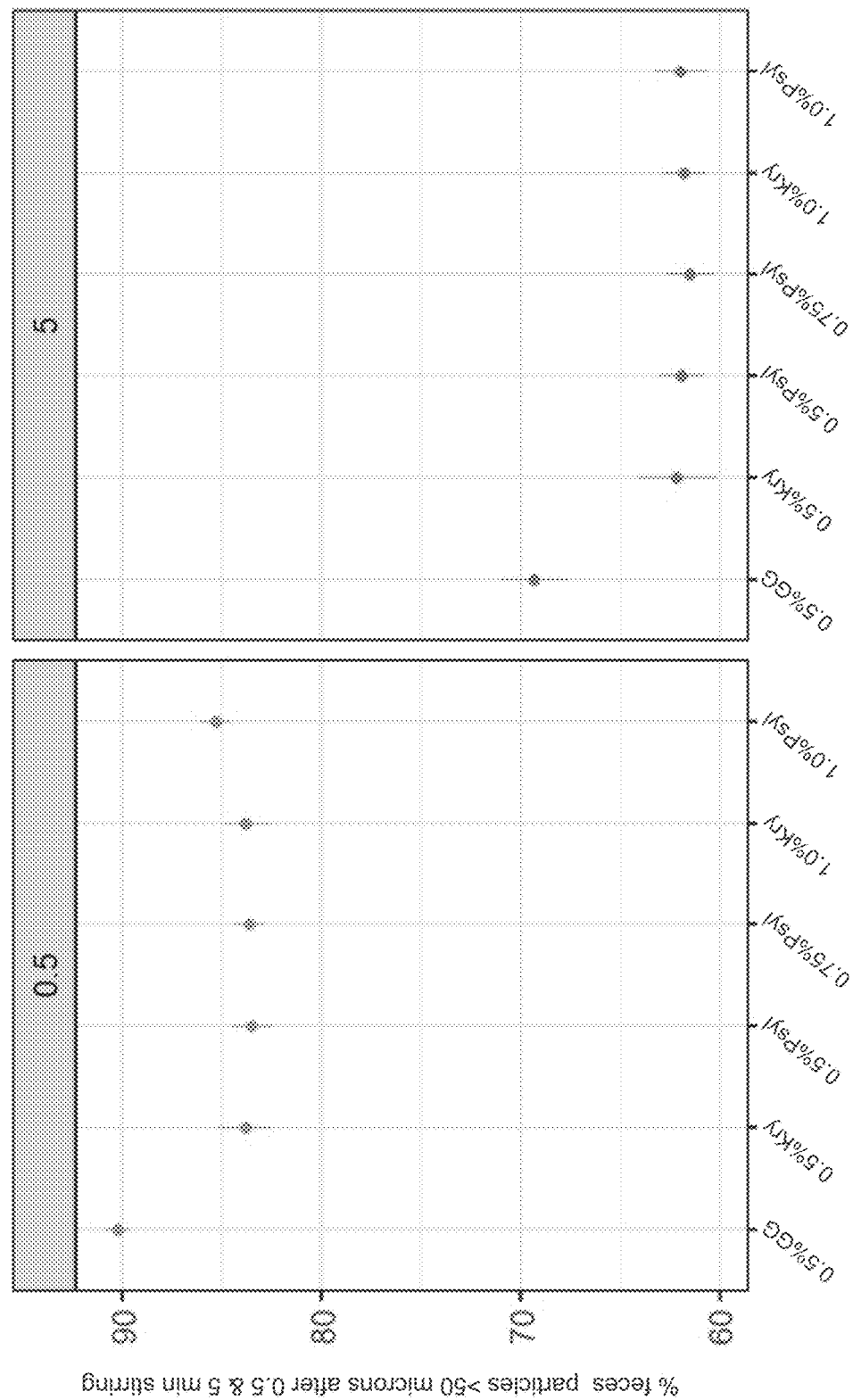
FIG. 17 shows percent of feces particles greater than 50 μm after 0.5 (left) and 5 (right) minutes of stirring in Mastersizer based on the fish feed formulations outlined in Example 9.

FIG. 17 shows the percent of feces particles greater than 50 μm after 0.5 minutes (left) and 5 minutes (right) of stirring at 2500 rpm. There was little or no estimated increase in feces particle size after 5 minutes of these diets containing psyllium and karaya gum compared to the fish-meal reference diet (FMRef) in Example 8 after accounting for the increase in percent of feces particles greater than 50 μm after 5 minutes for the same 0.5% guar gum diet fed in this example versus Example 8 (2.3 percentage point increase based on average of four tanks with three replicate samplings per tank).

Protein digestibility had only 0.5 percentage point range as feed median across diets. Fat digestibility was more variable across diets with 1.8 percentage point range as feed median but diets with highest 1.0% psyllium of diet (0.2 percentage point decrease) and 0.5% karaya gum of diet (1.1 percentage point decrease) had higher and more similar fat digestibility than feeds with lower inclusion of these binders compared to 0.5% guar gum reference diet that had highest fat digestibility. Dry matter digestibility had only 0.6 percentage point range as feed median across diets.

Example 10

The test feeds for this example are based on the reference diet base mix containing 55.8% protein and 20.1% fat. The detailed formulation of the reference diet base mix is given in Table 2 and diet formulations with binding agents in this Example are outlined in Table 31 and feed composition in Table 32. The extruded feeds had a pellet diameter of 4 mm.

TABLE 31

Diet formulations with binding agents.

| | % of diet (weight %) | | | | | |
|---|---|---|---|---|---|---|
| | 0.5% Gg | 0.3% Css | 0.3% LBG | 0.2% LBG & 3.33% GM | 0.1% LBG & 6.67% GM | 10% HiProGM |
| Guar Gum | 0.50 | | | | | |
| Cassia gum | | 0.30 | | | | |
| Locust bean gum | | | 0.30 | 0.20 | 0.10 | |
| Guar meal | | | | 3.33 | 6.67 | |
| High Protein Guar meal | | | | | | 10.00 |
| Fish meal | 71.49 | 71.65 | 71.65 | 68.98 | 66.31 | 63.63 |
| Wheat grain | 14.51 | 14.54 | 14.54 | 14.00 | 13.46 | 12.92 |
| Additives | 0.48 | 0.48 | 0.48 | 0.47 | 0.45 | 0.43 |
| Rapeseed oil | 6.51 | 6.51 | 6.51 | 6.51 | 6.51 | 6.51 |
| Fish oil | 6.51 | 6.51 | 6.51 | 6.51 | 6.51 | 6.51 |
| Total | 100.00 | 100.00 | 100.00 | 100.00 | 100.00 | 100.00 |

TABLE 32

Trial feed analyzed composition.

| | 0.5% Gg | 0.3% Css | 0.3% LBG | 0.2% LBG & 3.33% GM | 0.1% LBG & 6.67% GM | 10% HiProGM |
|---|---|---|---|---|---|---|
| Protein (%; Dumas) | 53.4 | 54.4 | 54.3 | 52.8 | 53.2 | 55.0 |
| Fat (%; LfNMR) | 19.8 | 19.7 | 20.4 | 20.6 | 19.7 | 20.0 |
| Moisture (%) | 7.5 | 5.5 | 6.4 | 7.5 | 7.9 | 6.5 |
| Ash (%) | 11.5 | 11.2 | 10.9 | 10.6 | 10.5 | 10.1 |
| Yttrium (mg/kg; XRF) | 114 | 143 | 135 | 128 | 111 | 114 |

Atlantic salmon were stocked in four replicate freshwater tanks per diet with 60 fish per tank and were about 406 g at time of feces sampling. Water temperature averaged 13.9° C. during the feces sampling week. Fresh feces were collected from each tank over three separate days after at least one week of acclimation feeding on trial diets. Feces binding was measured as a percentage of particles greater than 50 μm after 5 minutes of stirring as determined using laser diffraction on a Mastersizer. This measurement of feces binding represents the feces particles that can be removed by mechanical filtration. The particle size and digestibility analysis methods are the same as those outlined in Example 1.

Figure 18:
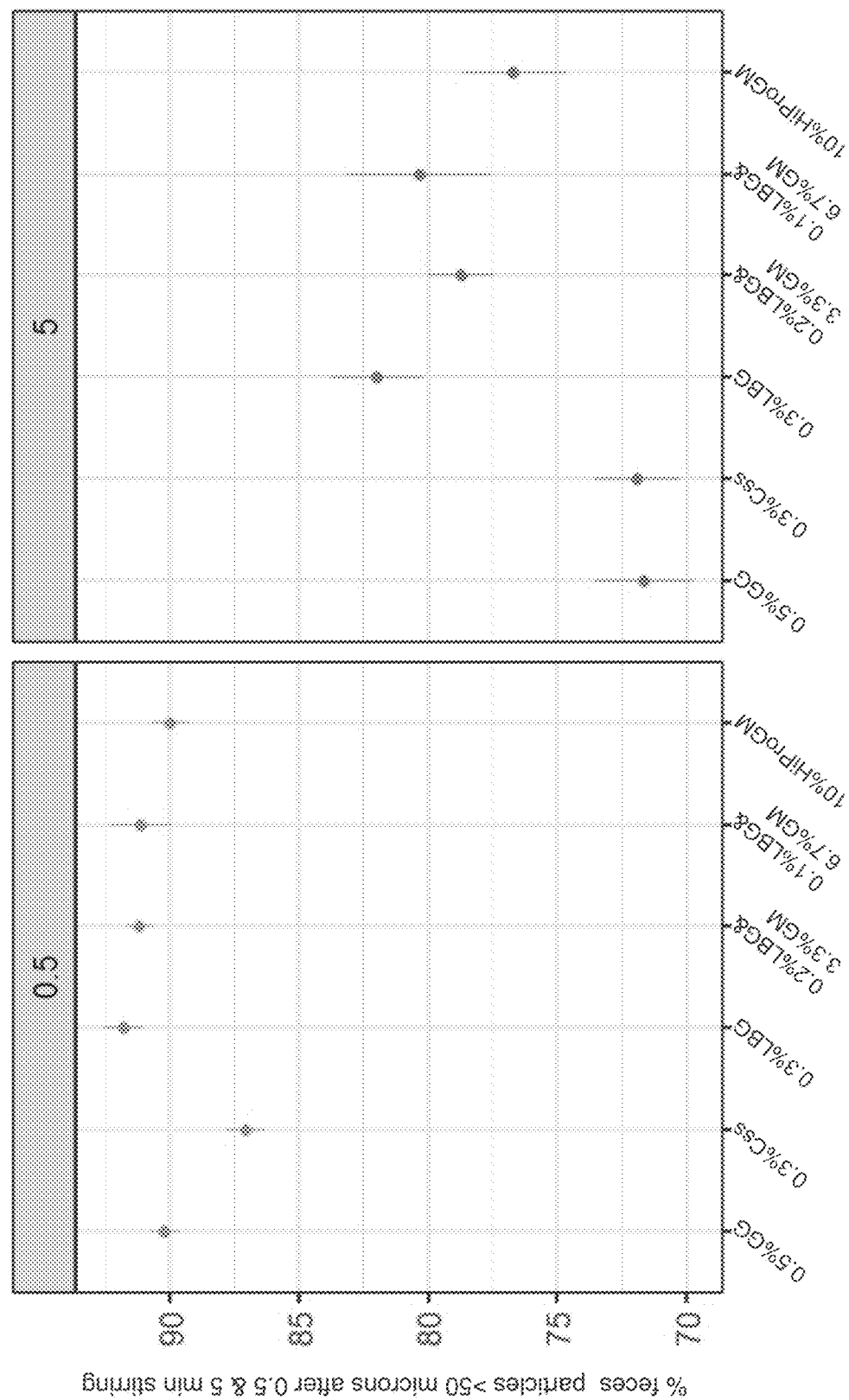
FIG. 18 shows percent of feces particles greater than 50 μm after 0.5 (left) and 5 (right) minutes of stirring in Mastersizer based on the fish feed formulations outlined in Example 10.

FIG. 18 shows the percent of feces particles greater than 50 μm after 0.5 minutes (left) and 5 minutes (right) of stirring at 2500 rpm. The 0.3% of cassia gum trial diet showed similar feces binding to the 0.5% guar gum trial diet. This confirms the assumptions in Example 8 that xanthan gum, added on top of 0.3% cassia gum, had little or no additional effect based on the calculated trend for feces particle size with cassia gum dosing up to 0.5%. The 0.3% locust bean gum trial diet gave much higher feces binding than the 0.3% cassia gum or the 0.5% guar gum trial diets. However, later information revealed that the batch of locus bean gum used was contaminated with ethylene oxide and recalled by the manufacturer after the completion of the trail Guar meal (GM; 56.6% protein; Dumas), combined with LBG, was also tested to give an estimated feces binding equivalent to 0.5% guar gum, based on the assumption that 10% guar meal or 0.3% LBG gives similar feces binding to 0.5% guar gum. However, these results show this to be an underestimate for the product batches tested in this trial given the much higher feces binding for combined 0.2% LBG/3.33% GM and 0.1% LBG/6.67% GM diets as compared to the 0.5% GG trial diet.

High protein GM (HiProGM; 68.5% protein; Dumas) was tested at 10% of diet. 10% high protein GM gave 76.7% of feces particles>50 microns after 5 min versus 75.9% in a diet with 10% guar meal (tested in another trial round with the same fish; data not shown) indicating similar feces binding for these batches of the two guar meal products.

Protein digestibility had a 1.7 percentage point range between diets with 0.5% percentage points for the 0.3% LBG diet as the largest protein digestibility decrease versus 0.5% GG diet based on feed median. Fat digestibility had a 2.2 percentage point range as feed median. Diet with 0.3% cassia gum had 0.6 percentage points lower fat digestibility than the 0.5% guar gum reference as feed median noting there was more similar fat digestibility (0.1 percentage point decrease) of 0.5% cassia gum versus 0.5% guar gum reference diets in Example 8. Diet with 0.3% locust bean gum had 0.5 percentage points lower fat digestibility than 0.5% guar gum reference but no negative effect of locust bean gum observed on fat digestibility when combined at 0.1 and 0.2% of diet with guar meal versus 0.5% guar gum reference based on feed median. Dry matter digestibility had 2.2% percentage point range between diets with a 0.7 percentage point reduction on dry matter digestibility for the 0.3% LBG diet as largest decrease compared to 0.5% GG diet based on feed average based on feed median. No negative digestibility effects observed for high protein guar meal versus 0.5% guar gum reference.

Example 11

The detailed formulations and analyzed composition of the diets used in this example are outlined in Table 12. The extruded feeds had a pellet diameter of 1.5 mm. The embodiments described in this example demonstrate the growth effects of cassia gum diets on small freshwater salmon.

TABLE 33

| Ingredient (% diet) | Ref | 0.25Css | 0.50Css | 0.75Css | 1.00Css | 0.50Gg |
|---|---|---|---|---|---|---|
| Marine meals | 29.1 | 29.0 | 28.8 | 29.0 | 29.1 | 28.8 |
| Plant meals | 54.7 | 54.6 | 54.4 | 54.0 | 53.7 | 54.4 |
| Additives | 3.4 | 3.5 | 3.5 | 3.5 | 3.5 | 3.5 |
| Fish oil | 6.4 | 6.4 | 6.4 | 6.4 | 6.4 | 6.4 |
| Rapeseed oil | 6.4 | 6.4 | 6.4 | 6.4 | 6.4 | 6.4 |
| Cassia gum | | 0.25 | 0.50 | 0.75 | 1.00 | |
| Guar gum | | | | | | 0.50 |
| Total | 100.0 | 100.0 | 100.0 | 100.0 | 100.0 | 100.0 |
| | | Diet composition | | | | |
| Protein (% diet; Dumas) | 52.7 | 52.5 | 52.9 | 52.6 | 52.6 | 52.4 |
| Fat (% diet; LF NMR) | 17.9 | 17.9 | 17.7 | 17.8 | 18.1 | 17.8 |

TABLE 33-continued

| Ingredient (% diet) | Ref | 0.25Css | 0.50Css | 0.75Css | 1.00Css | 0.50Gg |
|---|---|---|---|---|---|---|
| Moisture (% diet; NIR) | 7.6 | 7.7 | 7.4 | 7.2 | 6.7 | 7.9 |

Figure 19:
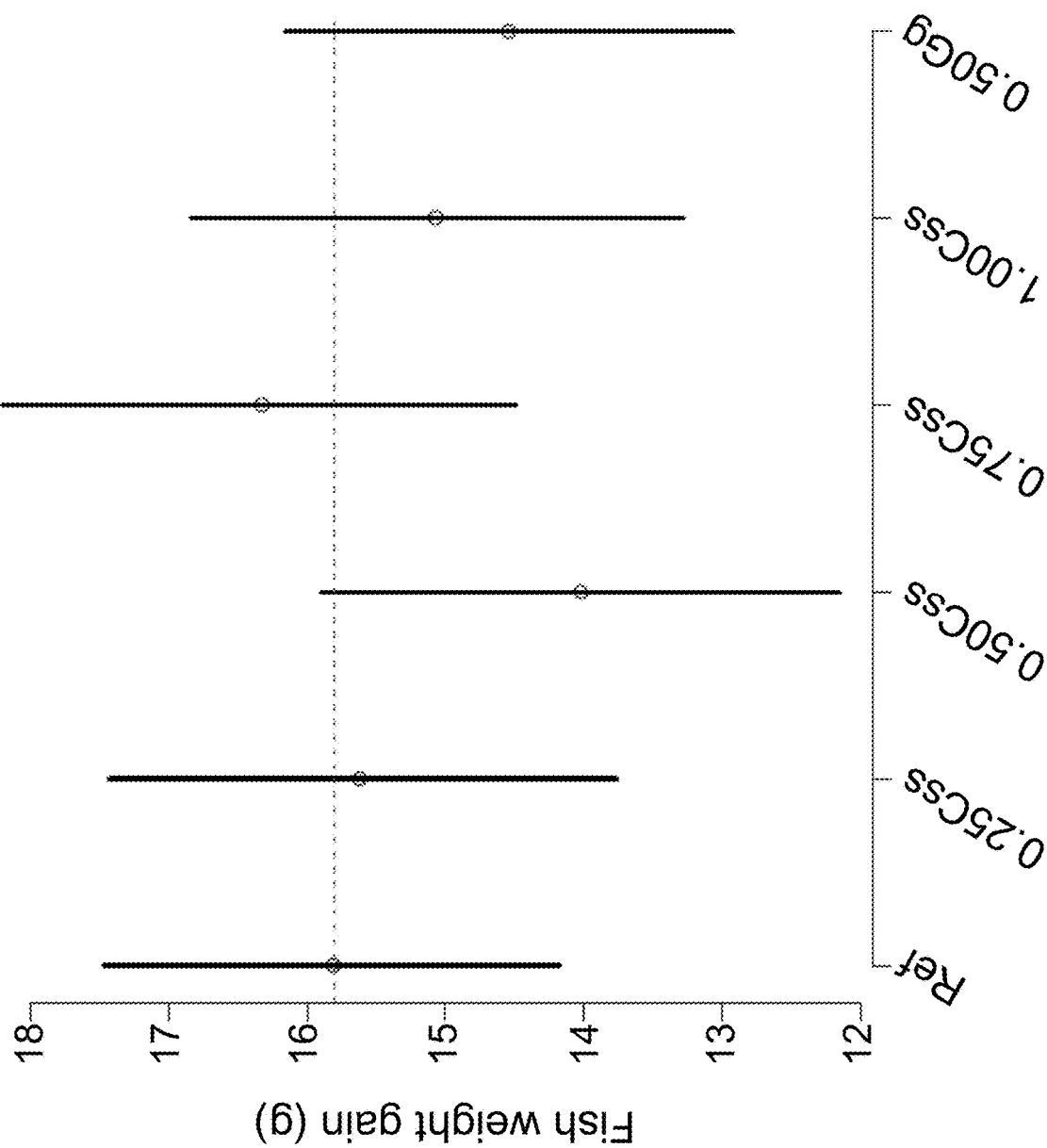
FIG. 19 shows fish weight gain in the fish of the trail outlined in Example 11.

Small Atlantic salmon were stocked in four replicate freshwater tanks for the reference (Ref) and 0.5% guar gum (0.5Gg; final fish weight missing for one tank) control diets and three replicate tanks for the cassia gum dose diets (0.25Css, 0.5Css, 0.75Css and 1.00Css) with 2.4 g initial fish weight and 80 fish per tank as overall tank averages monitoring fish weight gain over 8 weeks. Overall average fish weight was 17.7 g at the end of the 8 weeks. The temperature of the tanks averaged 13.9° C. Low mortalities were observed over the course of the trial with no more than two mortalities estimated per tank. There was no negative effect of cassia gum dose at up to 0.75% of diet on growth compared with either the Ref diet that had no feces binder or at up to 1.0% of diet compared with 0.5 Gg diet used as a feces binder control noting there was some variability in growth response within individual Cassia gum dose diets (See FIG. 19).

The invention claimed is:

1. A method for reducing suspended solids in rearing water of a fish farm, the method comprising feeding to a fish in the fish farm an extruded, pressed, or particulate fish feed comprising between about 0.2% to about 2.0% by weight of a feces binder selected from at least one of xanthan gum or a galactomannan polysaccharide comprising an average mannose to galactose ratio of 3:1 to 5:1, wherein suspended solids in the rearing water are reduced relative to the suspended solids in the rearing water of a fish fed a feed without the feces binder.

2. The method of claim 1, wherein the fish farm is a recirculation aquaculture system.

3. The method of claim 1, wherein suspended solids in the rearing water are reduced by at least 50% relative to the suspended solids in the rearing water of a fish fed a feed without the feces binder.

4. A method for increasing feces removal from a fish farm, the method comprising,
feeding to a fish in the fish farm an extruded, pressed, or particulate fish feed comprising between about 0.2% to about 2.0% by weight of a feces binder selected from at least one of xanthan gum or a galactomannan polysaccharide comprising an average mannose to galactose ratio of 3:1 to 5:1; and
removing or causing to have removed feces from the fish farm, wherein feces removal is increased relative to feces removal from an equivalent fish farm in which fish are fed a feed without the feces binder.

5. The method of claim 4, wherein the feces are removed by filtration or settling.

6. The method of claim 4, wherein the feces are removed by mechanical filtration with a pore size of 60 μm or less.

7. The method of claim 4, wherein the fish farm is a recirculation aquaculture system.

8. A method for increasing the size of feces particles produced by a fish in a fish farm, the method comprising feeding to the fish in the fish farm a fish feed comprising between about 0.2% to about 2.0% by weight of a feces binder selected from at least one of xanthan gum or a galactomannan polysaccharide comprising an average mannose to galactose ratio of 3:1 to 5:1, wherein the average size of feces particles produced by the fish in the fish farm is larger than the average size of feces particles produced by an equivalent fish that has been fed an equivalent feed lacking the feces binder.

9. The method of claim 8, wherein the galactomannan polysaccharide comprises tara gum, locust bean gum, cassia gum, or combinations thereof.

10. The method of claim 8, wherein the fish is a salmonid.

11. The method of claim 8, wherein the fish feed further comprises between about 15% and about 65% by weight protein and between about 10% and about 45% by weight fat.

12. The method of claim 8, wherein the fish feed further comprises land-animal protein, fishmeal, plant-based protein, or combinations thereof.

13. The method of claim 12, wherein the fish feed further comprises fishmeal and a land-animal protein.

14. The method of claim 12, wherein the fish feed further comprises fishmeal and a plant-based protein.

15. The method of claim 12, wherein the fish feed further comprises fishmeal, a land-animal protein, and a plant-based protein.

16. The method of claim 8, wherein the fish feed further comprises at least 0.1 mg astaxanthin per kg of feed.

17. The method of claim 8, wherein the fish feed comprises between 0.5% and 1.5% by weight of the feces binder.

18. The method of claim 8, wherein the fish feed comprises between 0.2% and 0.5% by weight of the feces binder.

19. The method of claim 8, wherein the fish feed comprises between 0.5% and 1.0% by weight of the feces binder.

20. The method of claim 8, wherein the fish farm is a recirculation aquaculture system.

21. The method of claim 8, wherein the feces with increased size also have increased mechanical strength and increased shear resistance.

22. The method of claim 8, wherein the feces size increases by at least 10%.

* * * * *